(12) United States Patent
Carty

(10) Patent No.: US 11,890,642 B2
(45) Date of Patent: Feb. 6, 2024

(54) SURFACE TREATMENT SYSTEM AND METHOD FOR SUBCUTANEOUS DEVICE

(71) Applicant: ConvaTec Technologies Inc., Las Vegas, NV (US)

(72) Inventor: Neal Robert Carty, Chicago, IL (US)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

(21) Appl. No.: 17/564,586

(22) Filed: Dec. 29, 2021

(65) Prior Publication Data

US 2022/0250114 A1 Aug. 11, 2022

Related U.S. Application Data

(63) Continuation of application No. PCT/US2021/065461, filed on Dec. 29, 2021.

(60) Provisional application No. 63/132,071, filed on Dec. 30, 2020.

(51) Int. Cl.
*A61L 24/00* (2006.01)
*B05D 3/14* (2006.01)
*A61L 31/10* (2006.01)

(52) U.S. Cl.
CPC .............. *B05D 3/142* (2013.01); *A61L 31/10* (2013.01); *A61L 2420/02* (2013.01)

(58) Field of Classification Search
CPC ........................... A61L 2420/02; B05D 3/141
USPC ................................................ 427/2.24, 2.25
See application file for complete search history.

(56) References Cited

U.S. PATENT DOCUMENTS

| 4,141,973 | A | | 2/1979 | Balazs | |
|---|---|---|---|---|---|
| 4,656,083 | A | * | 4/1987 | Hoffman | ............. A61L 33/0094 427/490 |
| 6,033,582 | A | * | 3/2000 | Lee | ........................... C23F 4/00 216/37 |
| 6,200,626 | B1 | * | 3/2001 | Grobe, III | ................ C08J 7/056 427/539 |

(Continued)

FOREIGN PATENT DOCUMENTS

| CA | 2673323 A1 | * | 7/2008 | ............. A61K 8/735 |
|---|---|---|---|---|
| EP | 2262550 B1 | | 8/2022 | |

(Continued)

OTHER PUBLICATIONS

Hirota et al. Coating of a surface with 2-methacryloyl-oxyethylphosphorylcholine (MPC) co-polymer significantly reduces retention of human pathogenic microorganisms. FEMS Microbiology Letters 248 (2005) pp. 37-45 (Year: 2005).*

(Continued)

*Primary Examiner* — Cachet I Proctor
(74) *Attorney, Agent, or Firm* — Taft Stettinius & Hollister LLP; Ryan O. White; Derek B. Lavender

(57) ABSTRACT

Methods of modifying a medical device and manufacturing a medical device are disclosed. One embodiment of a method of modifying a medical device includes treating a portion of the medical device with cold plasma and functionalizing the plasma-treated portion with a polymer. One embodiment of a method of manufacturing a medical device includes providing a subcutaneous part configured to be positioned subcutaneously in a user and performing a surface treatment on a portion of the subcutaneous part.

11 Claims, 13 Drawing Sheets

(56) References Cited

U.S. PATENT DOCUMENTS

| | | |
|---|---|---|
| 6,451,003 B1 | 9/2002 | Prosl et al. |
| 11,058,814 B2 | 7/2021 | Li et al. |
| 2007/0003603 A1 | 1/2007 | Karandikar et al. |
| 2007/0118211 A1* | 5/2007 | Gazza .................... A61L 29/16 623/1.42 |
| 2008/0003374 A1* | 1/2008 | Borra ...................... B05D 1/04 118/621 |
| 2008/0142038 A1* | 6/2008 | Kunzler ................ C08J 7/0427 134/1.1 |
| 2009/0065485 A1* | 3/2009 | O'Neill .................... H05H 1/46 219/121.48 |
| 2009/0118423 A1* | 5/2009 | Kumar .................... C08J 3/246 549/415 |
| 2010/0047532 A1* | 2/2010 | Mozetic .................. C08J 7/123 427/536 |
| 2010/0139663 A1* | 6/2010 | O'Neil ................ A61M 16/04 128/207.14 |
| 2010/0145286 A1* | 6/2010 | Zhang .................. A61L 17/005 525/453 |
| 2012/0046735 A1* | 2/2012 | Sill ........................ A61L 29/02 427/302 |
| 2018/0208735 A1* | 7/2018 | Nash ...................... B05D 3/144 |
| 2019/0217023 A1 | 7/2019 | Chattaraj et al. |

FOREIGN PATENT DOCUMENTS

| | | | | |
|---|---|---|---|---|
| GB | 2172295 A | 9/1986 | | |
| WO | WO-2006130122 A1 * | 12/2006 | ................ | C08J 7/12 |
| WO | 2018198051 A1 | 11/2018 | | |
| WO | 2019038378 A1 | 2/2019 | | |
| WO | 2019243631 A1 | 12/2019 | | |
| WO | 2020099434 A1 | 5/2020 | | |

OTHER PUBLICATIONS

International Search Report; International Searching Authority; International Patent Application No. PCT/US2022/014847; dated Mar. 15, 2022; 2 pages.

Written Opinion of the International Searching Authority; International Searching Authority; International Patent Application No. PCT/US2022/014847; dated Mar. 15, 2022; 5 pages.

Hirota et al. "Coating of a surface with 2-methacryloyloxyethyl phosphorylcholine {MPC} co-2, 7, 13, 17-18 polymer significantly reduces retention of human pathogenic microorganisms" FEMS Microbiology Letters. May 31, 2005 (May 31, 2005) vol. 248, p. 37-45.

* cited by examiner

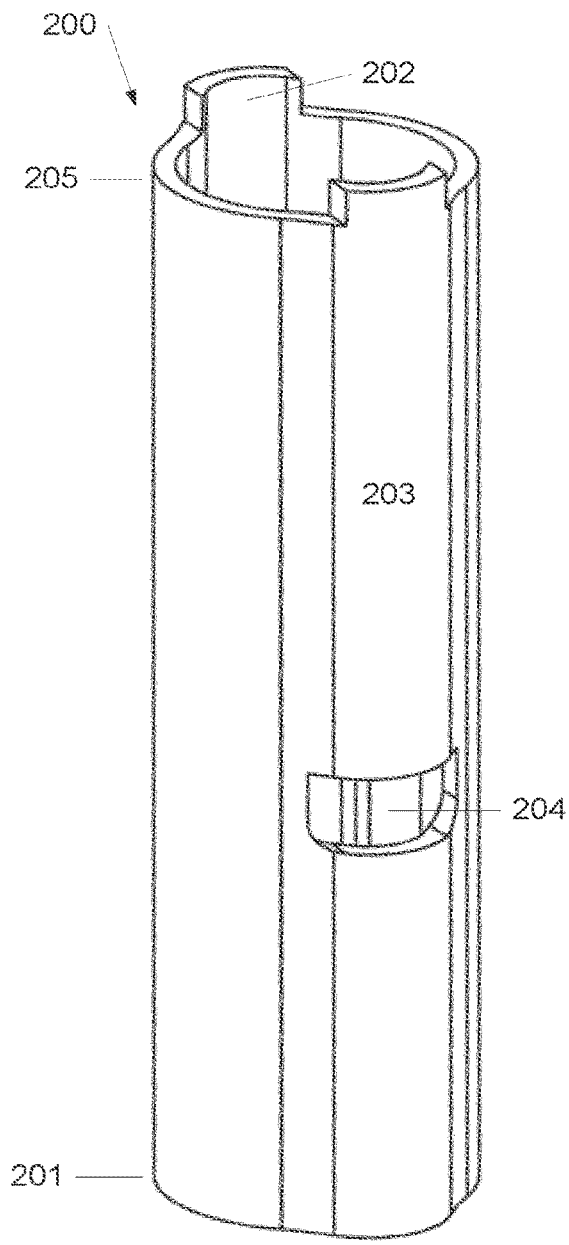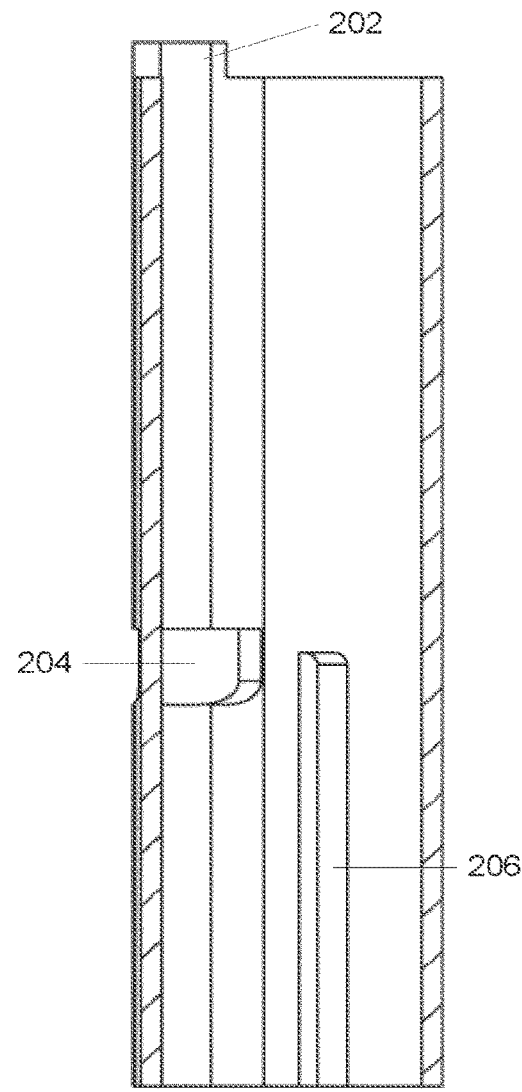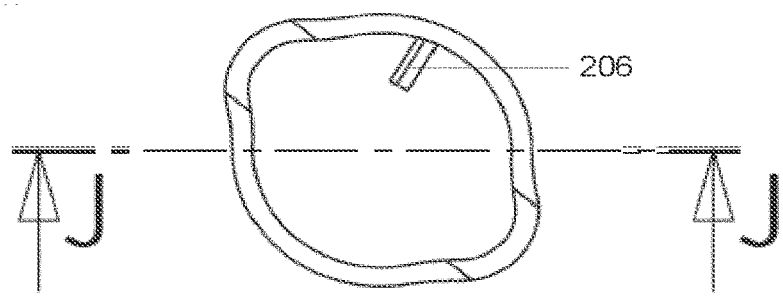
Fig. 2A
Fig. 2B
Fig. 2C

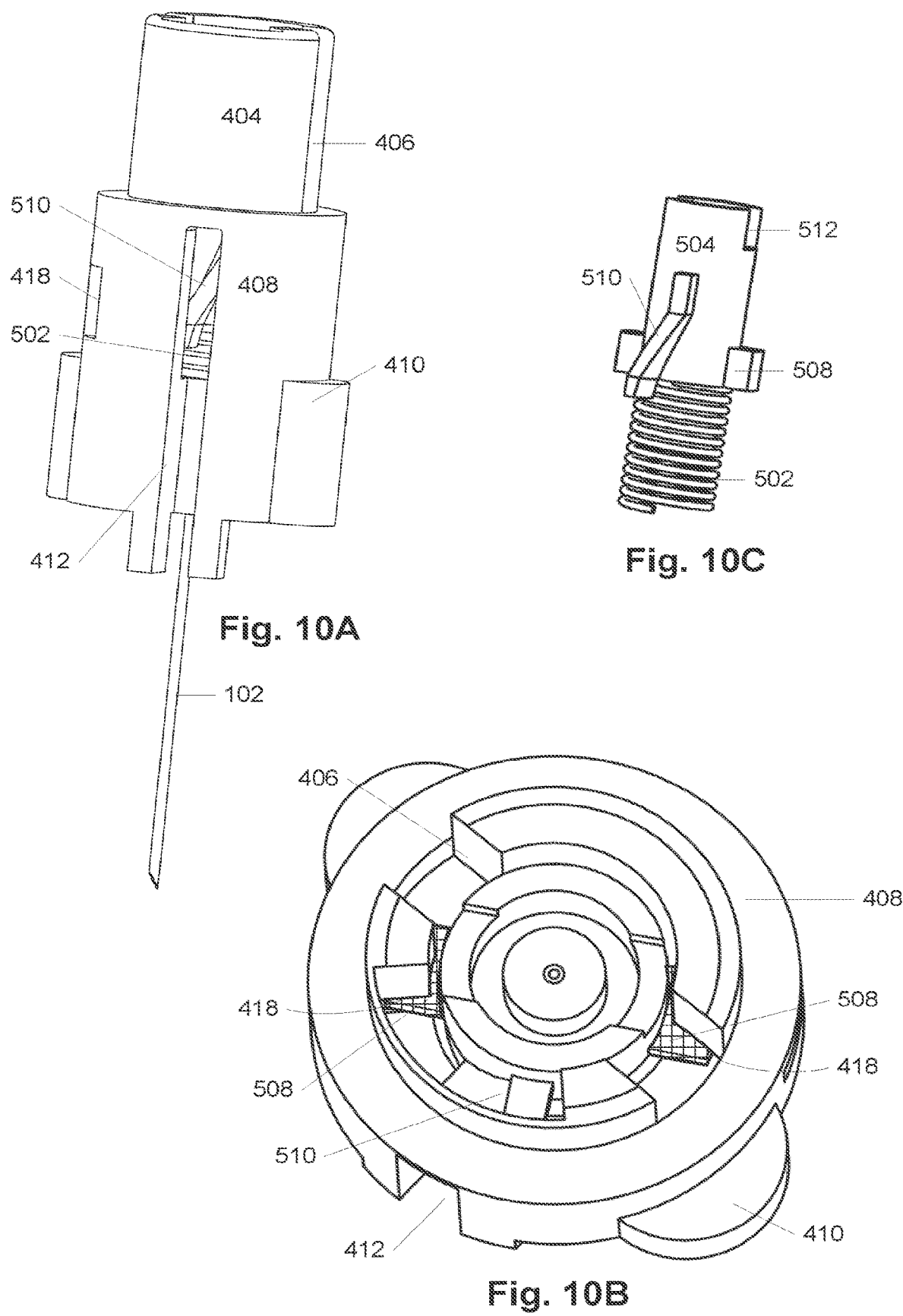

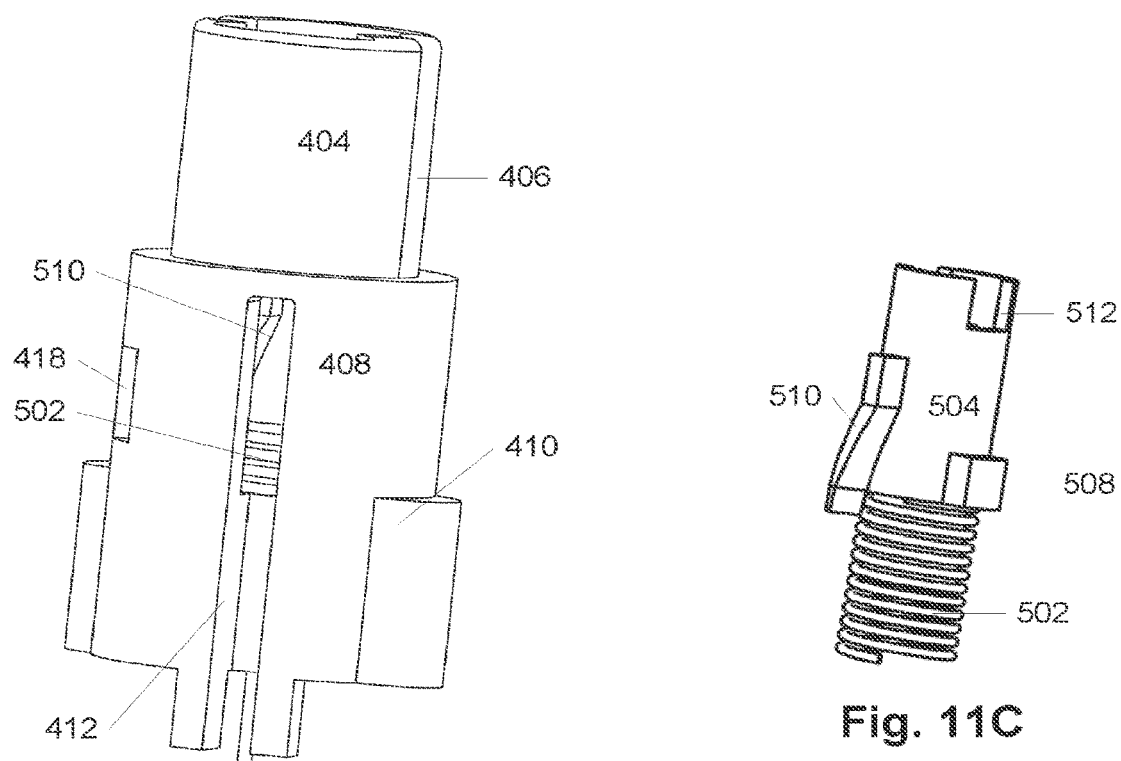
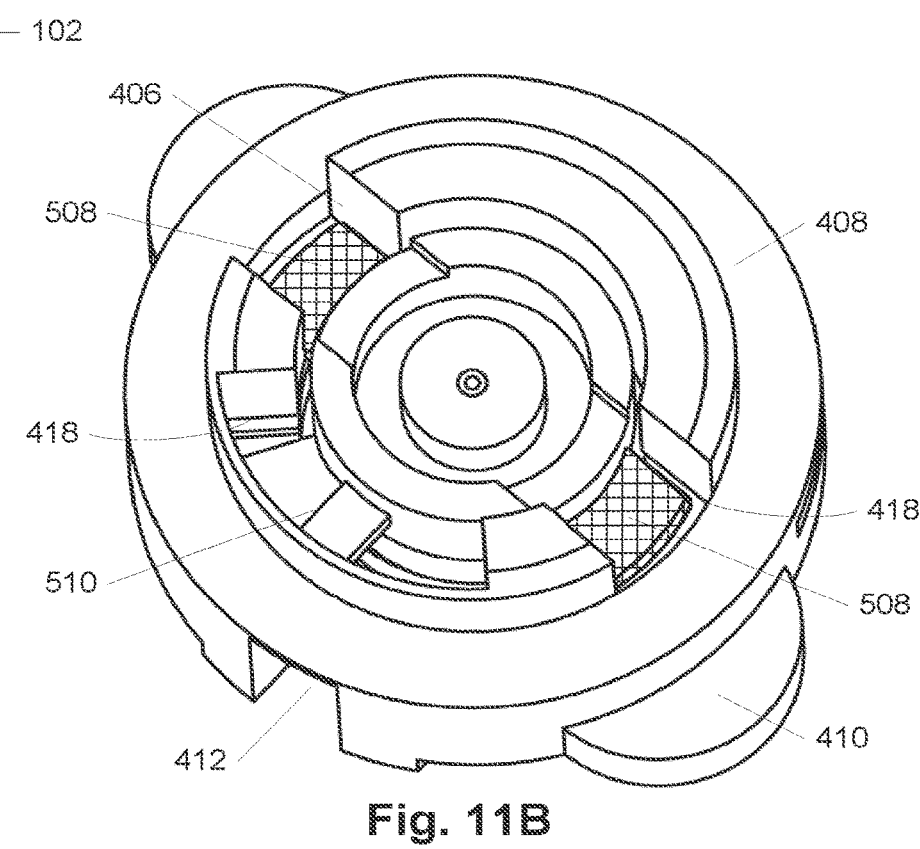

SURFACE TREATMENT SYSTEM AND METHOD FOR SUBCUTANEOUS DEVICE

CROSS-REFERENCE TO RELATED APPLICATION(S)

The present application claims priority to U.S. Provisional Patent Application No. 63/132,071 entitled "SURFACE TREATMENT SYSTEM AND METHOD FOR SUBCUTANEOUS DEVICE," which was filed on Dec. 30, 2020. The contents of that application are incorporated by reference herein in their entirety.

FIELD OF THE DISCLOSURE

The present disclosure relates to a subcutaneous device, and more specifically, to a subcutaneous device with a treated surface.

BACKGROUND OF THE DISCLOSURE

An inserter device, which may be referred to as an inserter or injector, may be used in the medical field for inserting medical devices (e.g., infusion sets, sensors, or the like) through the skin of a patient in a more or less automated fashion.

In some cases, when using an inserter, the user (e.g., a patient or a treatment provider) has to apply a force towards the surface of the user's skin to inject the medical device or a part of the medical device having the form of a needle, a cannula, a sensor, or the like. This may cause physiological or psychological distress and/or discomfort, and may lead to inappropriate application of the medical device. Many people are afraid of sharp objects, such as injection needles and other penetrating devices used for medical treatment and therapy, for example. This fear may be irrational and may hamper an appropriate medical treatment. In one example, in the case of self-medication, a lack of administration of an appropriate dose of a required medical composition may lead to potentially life-threatening complications. In another example, when treating diabetes (e.g., in juveniles), there is a risk that the required insulin dose may not be self-administered due to irrational fear of the insertion needle and/or a general lack of knowledge and awareness concerning the consequences of omitting the correct application of the device and dosage.

Another issue with insertion of medical devices may be the risk of contamination of the penetrating member before or during application. This may lead to an infection of the patient (e.g., through a contaminated insertion needle). The longer a needle is exposed, the higher the risk of accidental contamination, which may result from touching the needle with a finger, from bringing the needle in contact with an unclean surface, from airborne contamination, from aerosol contamination, or from the like. Depending on the nature of the contamination (e.g., contamination from a virus, bacteria, fungus, yeast, and/or prion) combined with the general health status of the patient, the resulting infection may rapidly turn into a life threatening situation.

Because contact with a contaminated insertion needle may be life-threatening, especially in hospital environments, the risk of accidental exposure to contaminated material in the form of a used insertion needle should be minimized. Thus, there is a need in the art for a robust, reliable, accurate, safe, hygienic, and user friendly inserter device, which addresses the issues discussed above.

Some inserter devices include a cannula and/or needle placed within a body section for insertion into the subcutaneous layer of skin. The cannula may remain in place for up to three days, or perhaps longer, at least in some cases. If the cannula remains in place longer than approximately three days in one location in the subcutaneous layer of skin, the patient's body may identify the cannula as a foreign body and respond by rejecting the cannula. The rejection of the foreign body may cause a reduction in absorption of any drug being administered through the cannula. As a result, it may be advantageous to provide a solution to allow for increasing the length of time it takes for a body to begin to reject the cannula. Even more, it may be desirable to provide a cannula and related components which may remain undetected by the patient's body while the cannula is subcutaneously inserted.

SUMMARY

The present disclosure may comprise one or more of the following features and combinations thereof.

According to one aspect of the present disclosure, a method of modifying a medical device may include treating a portion of the medical device with cold plasma and functionalizing the plasma-treated portion with a polymer.

In some embodiments, the polymer may include a zwitterionic polymer.

In some embodiments, the zwitterionic polymer may be a sulfobetaine polymer or a carboxybetaine polymer.

In some embodiments, the polymer may include a phosphorylcholine species.

In some embodiments, the polymer may include a compound having the formula:

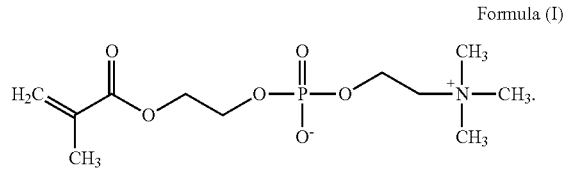 [SMILES: C=C(C)C(=O)OCCOP(=O)([O-])OCC[N+](C)(C)C]

Formula (I)

In some embodiments, the polymer may be a hyaluraonic acid species.

In some embodiments, the polymer may include a compound having the formula:

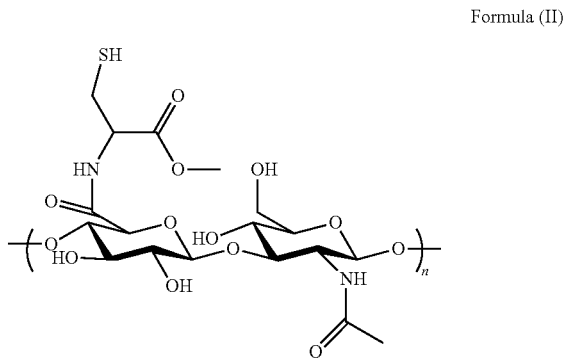

Formula (II)

In some embodiments, the plasma-treated portion of the medical device may be disposed at least partially along a surface of a subcutaneous part of the medical device that is configured for subcutaneous positioning in a user.

In some embodiments, the plasma-treated portion of the medical device may be at least partially defined along a surface of a cannula and configured for subcutaneous positioning in a user.

In some embodiments, the polymer may include a phosphorylcholine species, and the plasma-treated portion of the medical device may be at least partially defined along a surface of a cannula and configured for subcutaneous positioning in a user.

In some embodiments, the polymer may include a hyaluraonic acid species, and the plasma-treated portion of the medical device may be at least partially defined along a surface of a cannula and configured for subcutaneous positioning in a user.

In some embodiments, treating the portion of the medical device may include treating the portion at temperatures of about 0-60 degrees Celsius.

In some embodiments, treating the portion of the medical device may include treating the portion at pressures of around 1 atmosphere.

In some embodiments, treating the portion of the medical device may include treating the portion at temperatures of about 0-60 degrees Celsius and at pressures of around 1 atmosphere.

In some embodiments, functionalizing the plasma-treated portion with the polymer may include functionalizing the plasma-treated portion subsequent to treating the portion of the medical device.

In some embodiments, functionalizing the plasma-treated portion with the polymer may include functionalizing the plasma-treated portion simultaneously with treating the portion of the medical device.

In some embodiments, the method may include immobilizing a biomolecule through a linking molecule located on a surface of the plasma-treated treated portion by generating and maintaining a non-thermal atmospheric pressure plasma at a temperature at or below about 60° C., and the linking molecule may be deposited onto the plasma-treated portion by exposing the plasma-treated portion to a first plasma jet and the linking molecule to generate a linking layer on the plasma-treated portion.

In some embodiments, the method may include depositing the biomolecule onto the linking layer by exposing the linking layer to a second plasma jet and the biomolecule.

In some embodiments, the biomolecule may include a phosphorylcholine species.

In some embodiments, the biomolecule may include a compound having the formula:

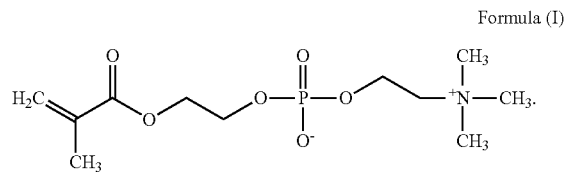 [SMILES: C=C(C)C(=O)OCCOP(=O)([O-])OCC[N+](C)(C)C]

Formula (I)

In some embodiments, the biomolecule may include a hyaluraonic acid species.

In some embodiments, the biomolecule may include a formulation compound having the formula:

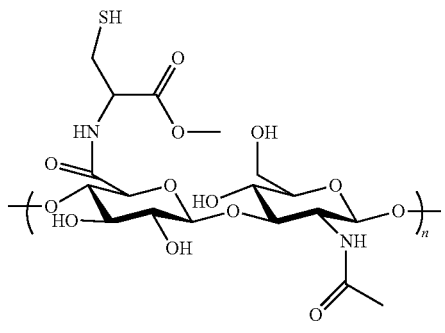

Formula (II)

In some embodiments, the polymer may include a methacrylated HLA.

In some embodiments, the polymer may include a methacrylated HLA compound having the formula:

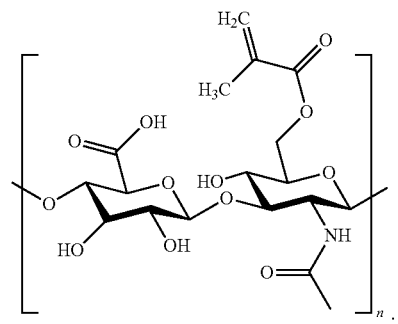

Formula (III)

In some embodiments, the polymer may include one or more hydrophilic polyalkylene glycol polymers.

In some embodiments, the one or more hydrophilic polyalkylene glycol polymers may include PEG or related PEG-like polymers with different architectures.

In some embodiments, the architectures may be one or more of networked, branched, dendritic, or hyperbranched.

According to another aspect of the present disclosure, a method of manufacturing a medical device may include providing a subcutaneous part configured to be positioned subcutaneously in a user and performing a surface treatment on a portion of the subcutaneous part. Performing a surface treatment on the portion of the subcutaneous part may include exposing a treated portion of the subcutaneous part to cold atmospheric plasma to create a linking layer thereon and functionalizing the linking layer with a biomolecule configured to reduce a foreign body response to the subcutaneous part when the subcutaneous part is subcutaneously positioned in the user.

In some embodiments, the method may include forming one or more apertures through the subcutaneous part prior to performing the surface treatment on the portion of the subcutaneous part, and performing the surface treatment on the portion of the subcutaneous part may not close the one or more apertures.

In some embodiments, the biomolecule may include a phosphorylcholine species.

In some embodiments, the biomolecule may include a compound having the formula:

Formula (I)

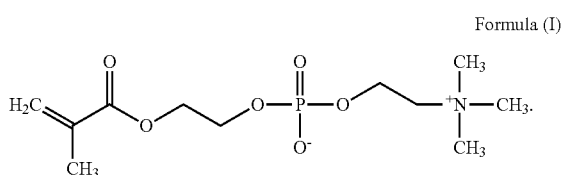

In some embodiments, the biomolecule may include a hyaluraonic acid species.

In some embodiments, the biomolecule may include a compound having the formula:

Formula (II)

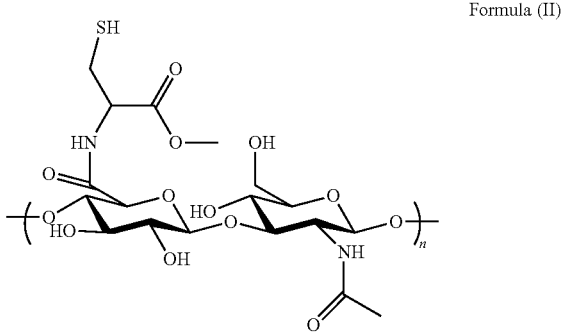

According to yet another aspect of the present disclosure, a method of manufacturing a medical device may include providing a subcutaneous part configured to be positioned subcutaneously in a user and performing a surface treatment on a portion of the subcutaneous part. Performing the surface treatment on the portion of the subcutaneous part may include exposing a treated portion of the subcutaneous part to cold atmospheric plasma to create a linking layer thereon, functionalizing the linking layer with a biomolecule configured to reduce a foreign body response to the subcutaneous part when the subcutaneous part is subcutaneously positioned in the user, and immobilizing the biomolecule through a linking molecule located on a surface of the treated portion.

In some embodiments, immobilizing the biomolecule through the linking molecule may include generating and maintaining a non-thermal atmospheric pressure plasma at a temperature at or below about 60° C.

In some embodiments, immobilizing the biomolecule through the linking molecule may include depositing the linking molecule onto the treated portion by exposing the treated portion to a first plasma jet and the linking molecule to generate the linking layer on the plasma-treated portion.

In some embodiments, the method may include depositing the biomolecule onto the linking layer by exposing the linking layer to a second plasma jet and the biomolecule.

In some embodiments, the method may include forming one or more apertures through the subcutaneous part prior to performing the surface treatment on the portion of the subcutaneous part, and performing the surface treatment on the portion of the subcutaneous part may not close the one or more apertures.

These and other features of the present disclosure will become more apparent from the following description of the illustrative embodiments.

BRIEF DESCRIPTION OF THE DRAWINGS

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

FIG. 2A is a front perspective view of a housing of the inserter device of FIG. 1;

FIG. 2B is a sectional view of the housing taken about axis J-J;

FIG. 2C is a end view of the housing from a proximal end thereof;

FIG. 10A is a perspective view of the first part and the second part of the inserter device of FIG. 1 in one state subsequent to insertion of an insertion needle;

FIG. 10B is a perspective end view of the first part and the second part of the inserter device of FIG. 1 in another state subsequent to insertion of the insertion needle;

FIG. 10C is a perspective view of the first part and the second part of the inserter device of FIG. 1 in yet another state subsequent to insertion of the insertion needle;

FIG. 11A is a perspective view of the first part and the second part of the inserter device of FIG. 1 in one state immediately prior to retraction of the insertion needle;

FIG. 11B is a perspective end view of the first part and the second part of the inserter device of FIG. 1 in another state immediately prior to retraction of the insertion needle;

FIG. 11C is a perspective view of the first part and the second part of the inserter device of FIG. 1 in yet another state immediately prior to retraction of the insertion needle;

DETAILED DESCRIPTION

Figure 1:
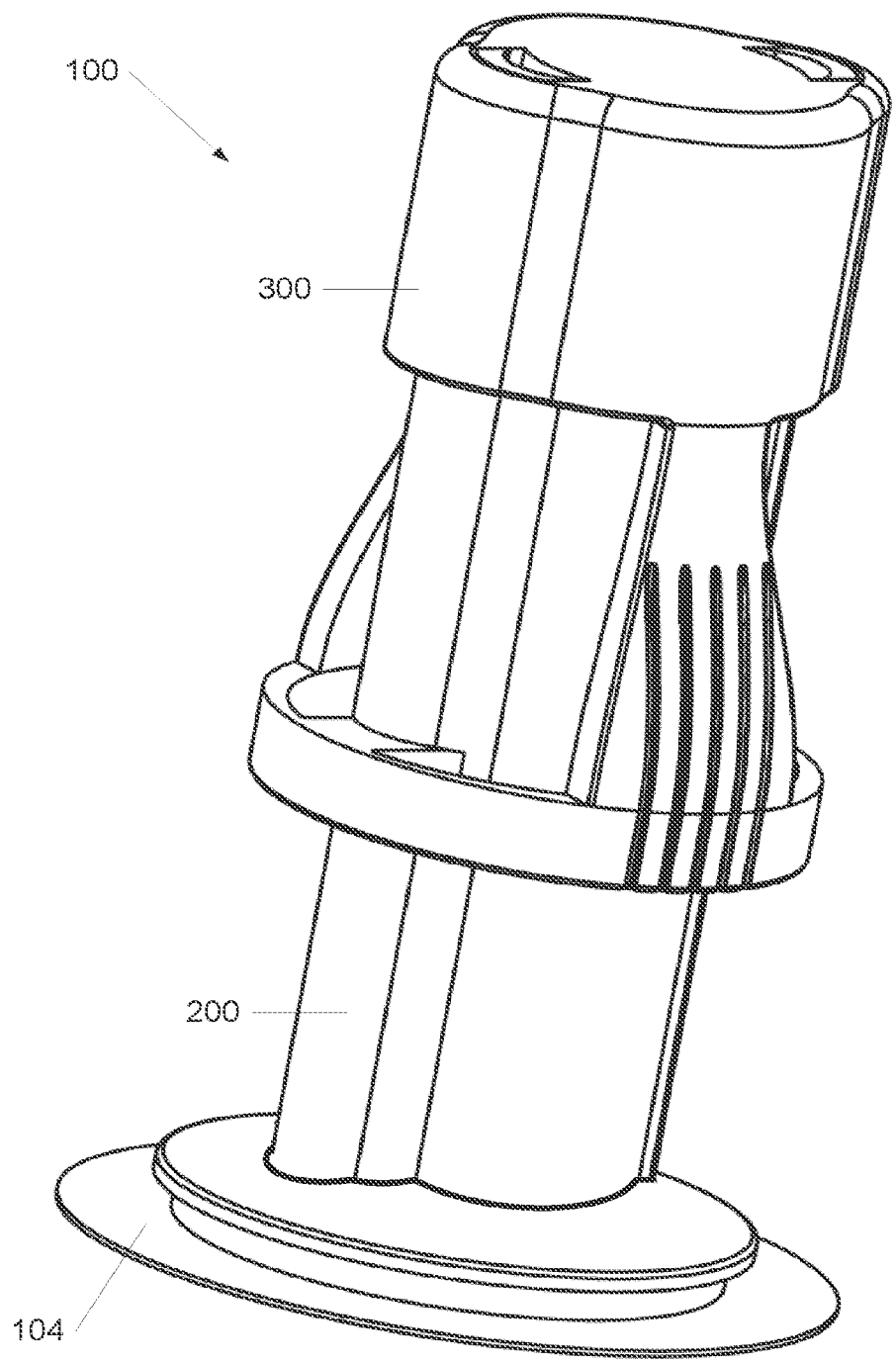
FIG. 1 is a perspective view of an assembled inserter device.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features, such as those representing devices, modules, instructions blocks and data elements, may be shown in specific arrangements and/or orderings for ease of description. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In some embodiments, schematic elements used to represent blocks of a method may be manually performed by a user. In other embodiments, implementation of those schematic elements may be automated using any suitable form of machine-readable instruction, such as software or firmware applications, programs, functions, modules, routines, processes, procedures, plug-ins, applets, widgets, code fragments and/or others, for example, and each such instruction may be implemented using any suitable programming language, library, application programming interface (API), and/or other software development tools. For instance, in some embodiments, the schematic elements may be implemented using Java, C++, and/or other programming languages. Similarly, schematic elements used to represent data or information may be implemented using any suitable electronic arrangement or structure, such as a register, data store, table, record, array, index, hash, map, tree, list, graph, file (of any file type), folder, directory, database, and/or others, for example.

Further, in the drawings, where connecting elements, such as solid or dashed lines or arrows, are used to illustrate a connection, relationship, or association between or among two or more other schematic elements, the absence of any such connection elements is not meant to imply that no connection, relationship, or association can exist. In other words, some connections, relationships, or associations between elements may not be shown in the drawings so as not to obscure the disclosure. In addition, for ease of illustration, a single connecting element may be used to represent multiple connections, relationships, or associations between elements. For example, where a connecting element represents a communication of signals, data or instructions, it should be understood by those skilled in the art that such element may represent one or multiple signal paths (e.g., a bus), as may be needed, to effect the communication.

Referring now to FIG. 1, an embodiment of an inserter device 100 having automatic insertion and automatic retraction of an insertion needle 102 is shown. The inserter device 100 is used for placing a port site 104 combined with a subcutaneous part 106 (see FIGS. 7-9) subcutaneously in a patient. The port site 104 may be used for injecting portions of medication over a time period, such as a time period of up to 3 days, at least in some embodiments. The port site 104 may include, or otherwise be embodied as, an infusion device, a sensor device, a patch device, or a similar device.

The inserter device 100 is shown in FIG. 1 in an assembled shelf state. In the illustrative embodiment, the inserter device 100 includes an outer part 300 and a housing 200, and the housing 200 is partly covered by the outer part 300. A functional part is accommodated inside the housing 200. The illustrative functional part includes a first part 400, a second part 500, an insertion spring 402, a retraction spring 502, and an insertion needle 102 attached to the second part 500. The inserter device 100 is adapted for use with a port site 104 (e.g., an infusion device) attached thereto, but it should be appreciated that other suitable port sites could also be used. Throughout the description, the term 'distal' refers to the end/surface/element farthest away from the port site 104 and the term 'proximal' refers to the end/surface/element closest to the port site 104. Additionally, for the purposes of the present disclosure, discussion of the 'vertical' plane/direction refers to the plane/direction extending parallel with the insertion needle 102, and discussion of the 'horizontal' plane/direction refers to the plane/direction parallel with the patient's skin surface that is perpendicular to the vertical plane/direction.

In the illustrative embodiment, FIG. 2A shows the housing 200 in a front view, FIG. 2B shows the housing 200 in a cut-through view along the axis J-J, and FIG. 2C shows the housing 200 in a view from the proximal end 201 of the housing 200. The shape and/or diameter of the proximal end 201 may have different designs depending on the port site 104 attached to the proximal end 201, and it should be appreciated that the invention is not limited to the shape and/or diameter depicted. Rather, the proximal end 201 may have various dimensions and take the shape of one or more suitable geometric forms depending on the port site 104.

The illustrative housing 200 includes, or is otherwise embodied as, an elongated tube comprising a sidewall 203 with an inner surface forming a cavity. The housing 200 has an oval shape to ensure that the first part 400 cannot rotate in the horizontal plane before, during, or after activation of the insertion device 100. Of course, in other embodiments, it should be appreciated that the housing 200 may take the shape of other suitable geometric forms.

The housing 200 illustratively includes two proximal protrusions 202 positioned opposite one another at the distal end 205 of the housing 200. The proximal protrusions 202 are adapted for engaging with (e.g., being received in) two corresponding openings 304 in the outer part 300. The housing 200 additionally includes two openings 204 positioned horizontally opposite one another approximately in the middle (e.g., lengthwise) of the housing 200. The openings 204 are adapted for engaging with locking elements 312 on the outer part 300. The proximal protrusions 202 and the openings 204 are aligned pairwise along vertical axes extending from the proximal end 201 to the distal end 205, thus extending in a direction parallel to the direction of insertion.

In the illustrative embodiment, on the inside of the housing 200, a housing guide member 206 is disposed that extends from the proximal end 201 to approximately the middle (e.g., lengthwise) of the housing 200. The housing guide member 206 extends along an axis parallel to the vertical axes defined by the pairs of proximal protrusions 202 and openings 204 and is circumferentially displaced approximately 80-110 degrees in relation thereto. The housing guide member 206 is adapted for being received by a slit 412 of the first part 400, and the housing guide member 206 is dimensioned such that when the guide member 206 is received in the slit 412, part of the guide member 206 extends through the slit 412 and into the interior of the first part 400.

Figure 3A:
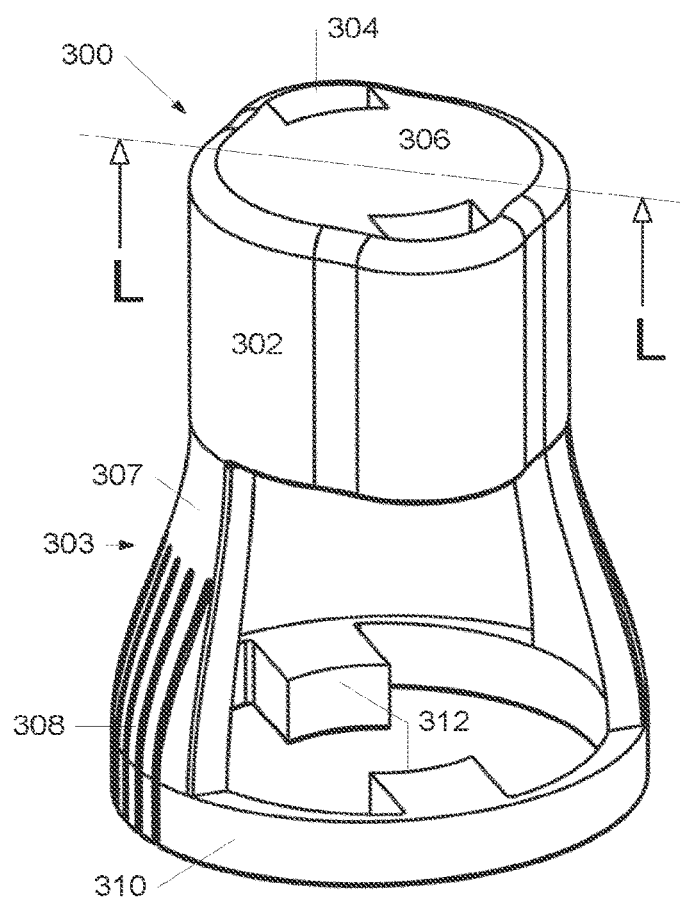
FIG. 3A is a front perspective view of an outer part of the inserter device of FIG. 1.
Figure 3B:
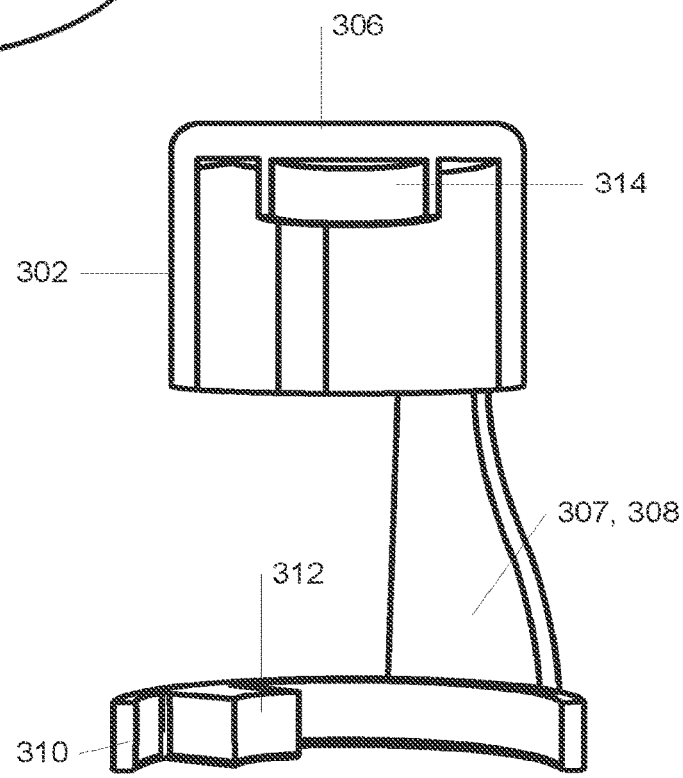
FIG. 3B is a sectional view of the outer part taken about axis L-L.

FIG. 3A illustrates a front view of the outer part 300 and FIG. 3B shows the outer part 300 in a cut-through view along the axis L-L. The outer part 300 illustratively includes, or is otherwise embodied as, a first section 302 and a second section 303. The first section 302 includes two openings 304 disposed at the distal end 306 of the first section 302. The two openings 304 are sized for interaction with the corresponding proximal protrusions 202 of the housing 200, thereby interlocking the housing 200 and the outer part 300. On the inside of the distal end 306, a protruding annular collar 314 is provided that is surrounded by a distal end of the insertion spring 402. As a result, the insertion spring 402 cannot be displaced horizontally before, during, or after insertion and/or retraction of the insertion needle 102.

The second section 303 illustratively includes two outwardly extending arms 307, an engaging device 310, release elements 308, and locking elements 312. The arms 307 are positioned opposite one another in the horizontal plane and are directly attached to the first section 302 at their distal ends. The engaging device 310 is illustratively embodied as a ring, which may be either circular or oval. Of course, in other embodiments, the engaging device 310 may take the shape of other suitable geometric forms. The release elements 308 extend partly along the arms 307 and partly along the engaging device 310.

In the illustrative embodiment, the locking elements 312 include two inwardly pointing parts for engaging with the openings 204 in the housing 200. The locking elements 312 are positioned opposite one another on the engaging device 310 and are circumferentially displaced approximately 90 degrees in relation to the release elements 308 and the arms 307. The locking elements 312 ensure that the insertion spring 402 stays in a pre-loaded position before activation of the inserter device 100 by engaging with corresponding locking members 410 on the first part 400, thereby fixing the first part 400 at the top of the distal end 205 of the housing 200 and on top of the locking elements 312.

Figure 4A:
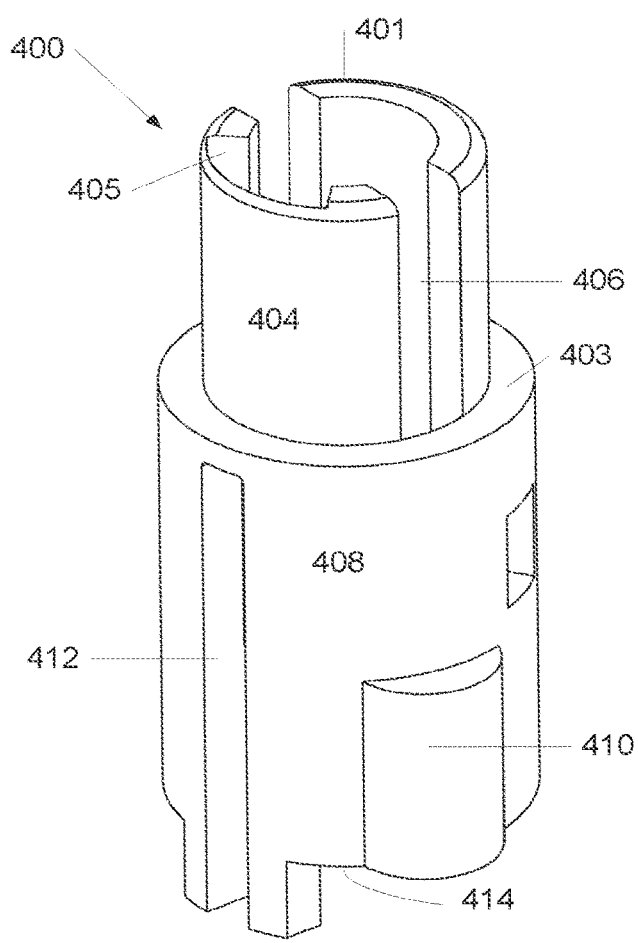
FIG. 4A is a front perspective view of a first part of the inserter device of FIG. 1.
Figure 4B:
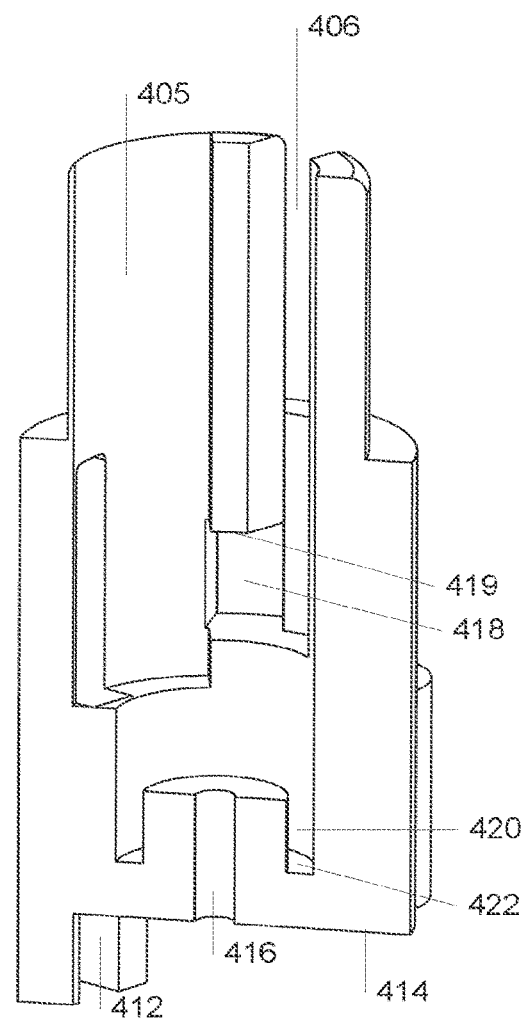
FIG. 4B is a sectional view of the first part taken about axis K-K.
Figure 4C:
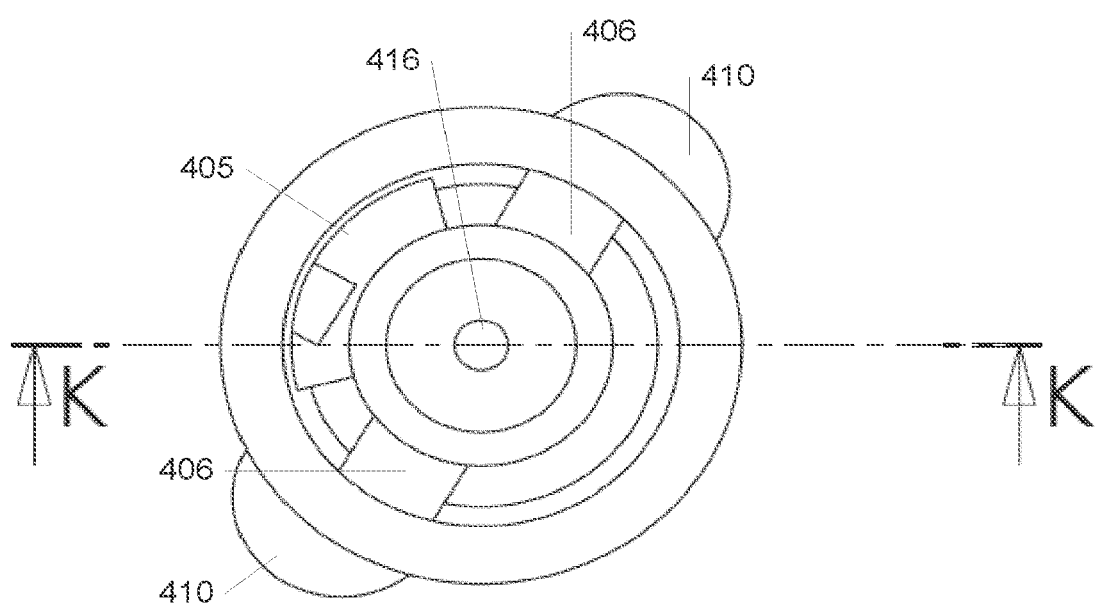
FIG. 4C is an end view of the outer part from a distal end thereof.

FIG. 4A illustrates the first part 400 in a front view, FIG. 4B illustrates the first part 400 in a cut-through view along the axis K-K, and FIG. 4C illustrates the first part 400 from the distal end 401 of the first part 400. The first part 400 illustratively includes a tube comprising a first section 404 and a second section 408. The outer diameter of the first section 404 is smaller than the outer diameter of the second section 408 such that a support surface 403 is formed. One end of the insertion spring 402 rests on the support surface 403.

The first section 404 illustratively includes two releasing slits 406 for engaging with corresponding locking members 508, 508' of the second part 500. The releasing slits 406 each extend from the distal end 401 along a vertical axis parallel to the insertion direction. The first section 404 further comprises a recess 405 on the inner surface to facilitate interaction with an inclining guide member 510 of the second part 500.

In the illustrative embodiment, the second section 408 has locking members 410 (e.g., two protrusions) arranged opposite one another in the horizontal plane on the outside of the second section 408. In the pre-loaded shelf position shown in FIG. 7, the locking members 410 are engaging with the locking elements 312 of the outer part 300. That interaction secures the insertion spring 402 in the pre-loaded position to prevent the insertion needle 102 from being activated during transportation. Between the two locking members 410, a slit 412 is arranged for receiving the inner housing guide member 206 of the housing 200 during activation of the inserter device 100.

The illustrative proximal surface 414 of the first part 400 is provided with a central annular opening 416 (see FIGS. 4B and 7) through which the insertion needle 102 may pass when inserting the subcutaneous part 106 in a patient. The opening 416 is illustratively sized to allow only the insertion needle 102 to pass through. In some cases, the diameter of the opening 416 is only 10-20% larger than the diameter of the insertion needle 102. This is advantageous to prevent a user from accidently putting a finger through the opening 416 and contacting with the insertion needle 102 in use of the device 100. Further, due to a small opening 416, the insertion needle 102 is hardly visible, which may have a positive psychological effect on patients/users that are afraid of needles.

Openings 418 are illustratively disposed on the inside of the second section 408 for engaging with corresponding locking members 508, 508' of the second part 500. In the shelf and the insertion positions, the locking members 508, 508' of the second part 500 are supported by a support rim 419, thereby fixing the retraction spring 502 and the second part 500 in the pre-loaded state. An annular recess 420 (see FIGS. 4B and 7) is provided on the surface 422 of the proximal end accommodating one end of the retraction spring 502, thereby ensuring that it cannot be displaces horizontally before, during, or after insertion and/or retraction.

Upon insertion of the insertion needle 102, in the illustrative embodiment, the proximal surface 414 applies a pressure to the subcutaneous part 106 and thereby locks the subcutaneous body part 110 inside a cavity of the port site 104. Further, since the first part 400 presses against the distal surface 114 of the subcutaneous part 106 due to the relaxed insertion spring 402 after insertion of the insertion needle 102, the proximal surface 414 assists in releasing the subcutaneous part 106 from the insertion needle 102 as the insertion needle 102 is retracted into the inserter device 100.

Optionally, in some embodiments, the first part 400 may be provided with additional mechanisms for releasing the subcutaneous part 106 from the insertion needle 102. In one example, those mechanism(s) may take the form of a distance piece, which assures that the subcutaneous part 106 is pushed down into the opening of the base 104 with such a force that the subcutaneous part 106 contacts, or is positioned past, a locking mechanism inside the opening of the base 104. In particular, one mechanism for releasing the subcutaneous part 106 includes a flat spring arranged between the proximal surface 414 of the first part 400 and the distal surface 114 of the subcutaneous part 106. The flat spring is attached to or is a part of the first part 400 at one end, at least in some embodiments. As the first part 400 is pushed down towards the base 104 by the insertion spring 402, the flat spring will be loaded as the first part 400 gets close enough to the base 104. The flat spring will then apply a pressure to the subcutaneous part 106 to lock the subcutaneous body part 100 inside the opening of the base 104.

Figure 5A:
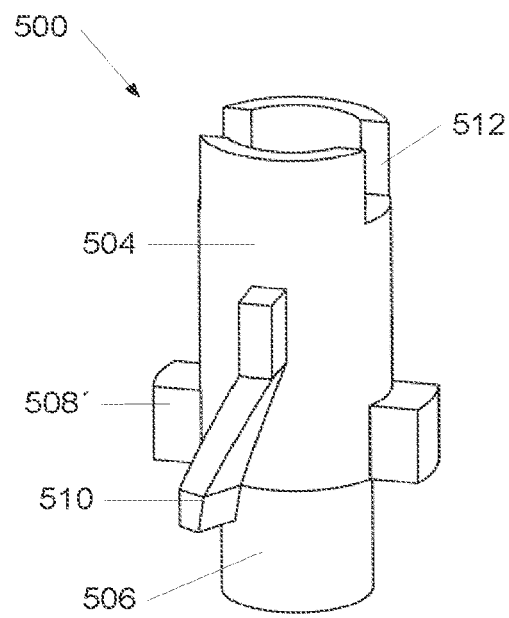
FIG. 5A is a front perspective view of a second part of the inserter device of FIG. 1.
Figure 5B:
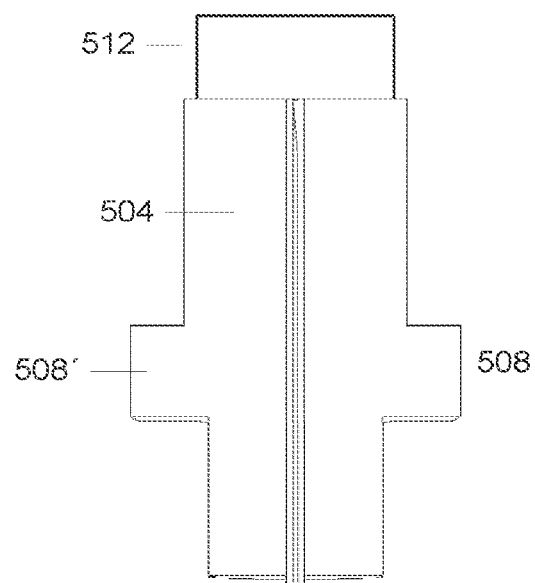
FIG. 5B is a sectional view of the second part taken about an axis connecting locking members of the second part.

FIG. 5A illustrates the second part 500 in a front view and FIG. 5B illustrates the second part 500 in a cut-through view along the axis connecting the locking members 508, 508'. The second part 500 includes a relatively small elongated tube sized to fit inside the first part 400. The second part 500 includes a first section 504 and a second section 506. The outer diameter of the first section 504 is larger than the diameter of the second section 506 to form a support surface for accommodating one end of the retraction spring 502 as shown in FIGS. 10C and 11C, thereby ensuring that the retraction spring 502 remains positioned around the second section 506 at one end at all times.

The locking members 508, 508' (in this embodiment two protrusions) illustratively arranged on the outside of the first section 504 are configured to slide inside the corresponding releasing slits 406 in the first part 400 during activation of the inserter device 100. In between the locking members 508, 508' is the inclining guide member 510. The second part 500 includes recesses 512 for guiding the second part 500 relative to the first part 400 during use of the inserter device 100. The insertion needle 102 is attached to the second part 500 and extends vertically upward inside the normally solid second part 500. Of course, it should be appreciated that in some embodiments, the positions of the first part 400 and the second part 500 could be reversed.

Figure 6:
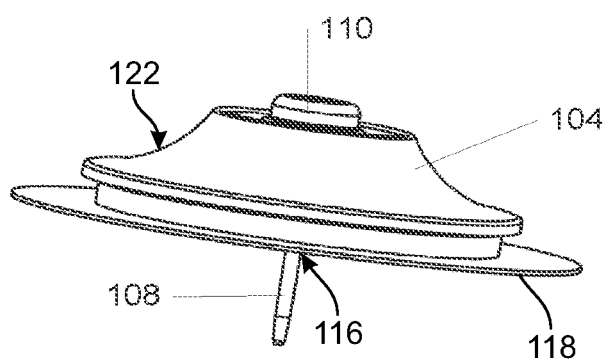
FIG. 6 is a perspective view of an embodiment of a port site adapted for use with the inserter device of FIG. 1.

FIG. 6 depicts an embodiment of the illustrative port site 104 (e.g., an infusion port) in which the subcutaneous part 106 includes a cannula 108 and a body part 110. The body part 110 is shaped to secure the subcutaneous part 106 in the port site 104 upon insertion of the subcutaneous part 106 in the patient's skin 112. The subcutaneous part 106 is positioned on the insertion needle 102 and kept in position due to friction between the insertion needle 102 and the soft contact parts of the subcutaneous part 106, such as the cannula 108, for example. The insertion needle 102 may be located inside, alongside, or outside the cannula 108.

In some embodiments, one or more surfaces of the port site 104 and/or the subcutaneous part 106 may include a treated portion 116. The treated portion 116 may be disposed along a surface of the port site 104 and/or the subcutaneous part 106 that directly contacts the user and/or is positioned subcutaneously in the user. The treated portion 116 may undergo a surface treatment process to introduce special performance characteristics into the treated portion 116. Consequently, interfacial phenomena (e.g., lubricity, wettability, or adhesiveness) may be controlled without modifying bulk properties of the underlying parts 104, 106, such as tensile strength or flexibility, for example. The surface treatment process may be a cost-effective mechanism for incorporating active agents such as drugs, antimicrobial agents, or peptides in minimal quantities that are localized only to the surfaces where they are needed (i.e., the treated portion 116). For the subcutaneous part 106, the treated portion 116 may include a polymeric form to render the subcutaneous part 106 less susceptible to foreign body response and thereby increase tolerability over longer wear times.

In one aspect of this disclosure, the surface treatment process for the treated portion 116 may utilize cold atmospheric plasma. The cold atmospheric plasma surface treatment process may provide a surface treatment process that is versatile and implemented in mild process conditions. For example, cold atmospheric plasma may operate with low energy at room temperature (i.e., about 10-30 degrees Celsius) and atmospheric conditions (i.e., 1 atmosphere of pressure, no vacuum). Accordingly, as used herein, the term "surface treatment process" includes any cold atmospheric plasma process. One example contemplated herein implements a two-step method for the immobilization of a biomolecule through a linking molecule on the surface of the treated portion 116 by generating and maintaining a nonthermal atmospheric pressure plasma at a temperature between about room temperature and about 60° C. In one embodiment, the biomolecule may be a biopolymer or biocompatible polymer.

Cold plasma, which may be referred to as non-thermal or non-equilibrium plasma, refers to cold temperature plasma formation at atmospheric pressures. It should be appreciated that cold plasma is a plasma which is not in thermodynamic equilibrium because the electron temperature is hotter than the temperature of heavy species (e.g., ions and neutrals) in the plasma. In some cases, cold plasma may be created when a sufficient amount of energy (e.g., higher than the ionization energy) is added to gaseous atoms and/or molecules, causing ionization and subsequently generating free electrons, photons, free radicals, and ionic species. The excitation energy supplied to a gas to form a cold plasma may originate from electrical discharges, direct currents, radio frequencies, microwaves, or other forms of electromagnetic radiation. By selecting the reaction conditions accordingly (e.g., activation energy, pressure, power input, carrier gases, and initial organic compounds such as polymer or monomers), suitable modified surfaces may be created for different applications or requirements. Non-limiting examples of cold plasma technologies and methodologies for generating cold plasma include atmospheric pressure plasma jet, dielectric barrier discharge, direct current (DC) glow discharge, electrical discharge plasma, microwave discharge, pulsed power discharge, radiofrequency (RF) discharge, and the like.

Polymerization of the surface in any of the embodiments described herein may include, or otherwise be embodied as, any suitable polymerization process, such as conventional condensation, addition or free radical graft polymerization (FRGP), or controlled radical polymerization (CRP) (e.g., ATRGP, RAFT, or NMGP). The surface activity may be controlled by adjusting the plasma operating parameters such as the plasma source, plasma precursor and carrier gas, gas flow rate, gas partial pressure, high frequency power, and applied voltage, as well as the preparation of the surface treatment time and substrate surface.

In some embodiments, the cold plasma is cold atmospheric plasma (CAP). The cold plasma is an atmospheric pressure discharge cold plasma, at least in some embodiments.

In some embodiments, the cold atmospheric plasma is at a pressure of between around 50 kPa and 150 kPa. Additionally, in some embodiments, the CAP is at a pressure of between around 60 kPa and 140 kPa, between around 70 kPa and 130 kPa, or between around 80 kPa and 120 kPa. Further, in some embodiments, the CAP is at a pressure of between around 100 kPa and 103 kPa. In other embodiments, however, the cold plasma may be applied under reduced pressure, such as below 50 kPa (e.g., between 0.01 kPa and 40 kPa or between 0.1 kPa and 25 kPa).

In some embodiments, a cold plasma stream is applied to the surface to cause the formation of surface-bound active sites that function as polymerization initiators or covalent binding sites. When contacted with a polymer, monomer, or monomer solution, the active sites may facilitate formation of a dense array of graft polymers covalently bound to the substrate surface, at least in some embodiments.

The surface of the medical device (e.g., the inserter device 100) may be placed either directly into contact with the plasma as it is generated, or in a separate post-plasma area. If the surface is placed directly in contact with the plasma during generation, such placement may occur in a plasma reactor. For the purposes of the present disclosure, a post-plasma (post-discharge) area refers to an area outside of the plasma that is located downstream of a plasma forming gas flow in which reactive species such as radicals are still present. That post-plasma area is particularly useful for delicate substrate surfaces such as polymers.

The cold plasma treatment may be performed at an RF power of at least 1 W, 5 W, 10 W, 15 W, or at least 20 W, at least in some embodiments. Additionally, in some embodiments, the cold plasma treatment may be performed at an RF power of no more than 2000 W, 1500 W, 1000 W, 500 W, 400 W, 300 W, 200 W, 100 W, 90 W, 80 W, 70 W, or no more than 60 W. Furthermore, in some embodiments, the treatment may be performed at an RF power of about 20 to 60 W.

The temperature of the cold plasma may be at least 5° C. or at least 10° C., in some embodiments. The temperature of the cold plasma may be no more than 60° C. or no more than 50° C., at least in some embodiments. Further, in some embodiments, the cold plasma is at ambient temperature, such as between 15° C. and 35° C., for example.

In some embodiments, the cold plasma treatment may be performed for at least 1 second, 2 seconds, 3 seconds, 4 seconds, 5 seconds, or at least 10 seconds. Additionally, in some embodiments, the cold plasma treatment may be performed for no more than 240 seconds, 180 seconds, or no more than 120 seconds. Further, in some embodiments, the treatment may be performed for about 5 to 120 seconds.

In some embodiments, the cold plasma treatment may be performed at an RF power of between about 10 W to about 60 W and for a period of between about 5 seconds to about 120 seconds. Additionally, in some embodiments, the cold plasma treatment may be performed using the aforesaid RF and time ranges with a precursor gas selected from the group including hydrogen, oxygen, nitrogen, argon, or helium.

Figure 12:
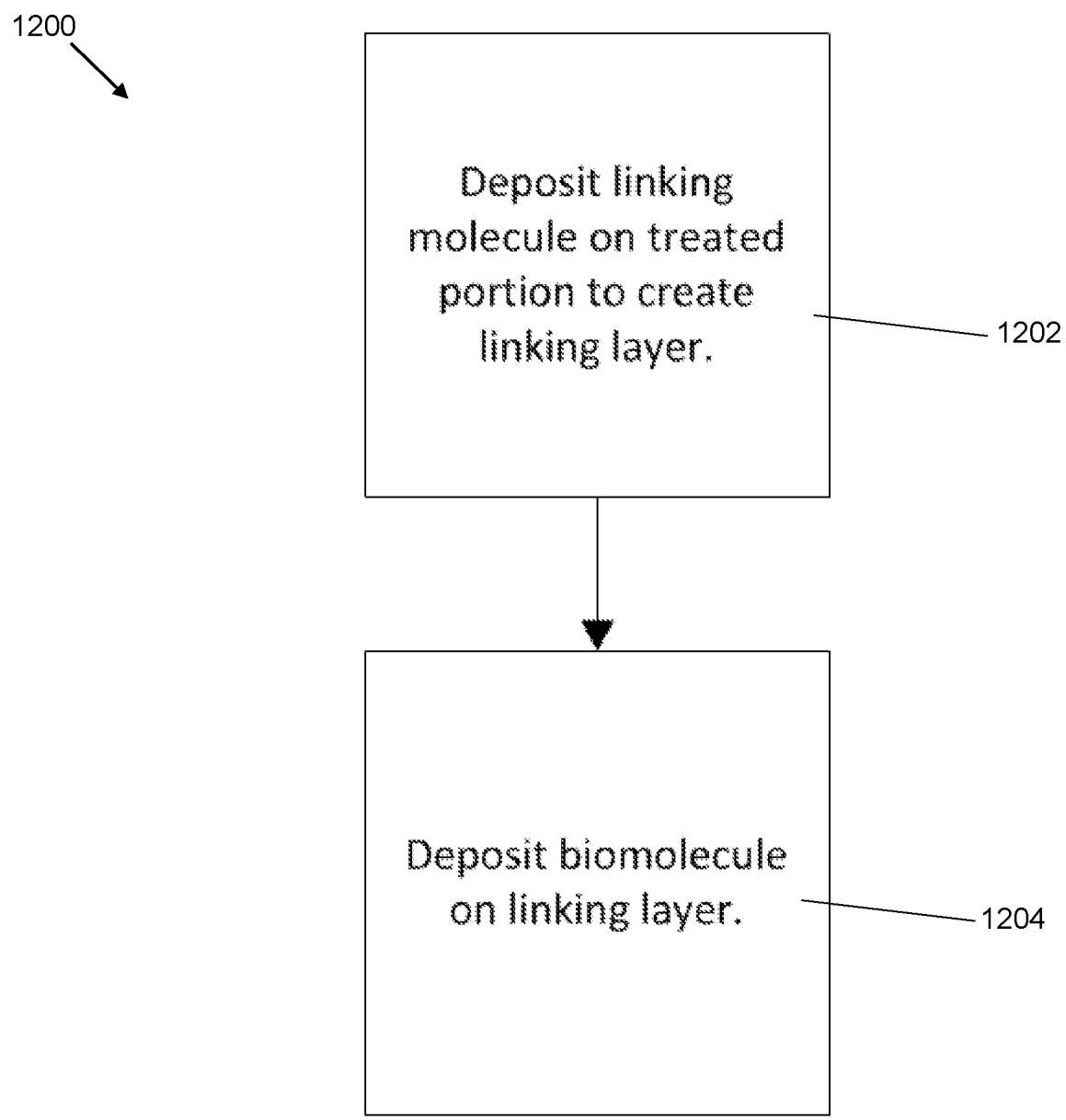
FIG. 12 is a simplified flowchart of a surface treatment method.

In one embodiment illustrated in FIG. 12, the surface treatment process 1200 includes a first block 1202 and a second block 1204, which may be sequentially or simultaneously carried out. In the first block 1202, the linking molecule is deposited onto the treated portion 116 through exposing the treated portion 116 to a first plasma jet and the linking molecule, thereby generating a linking layer on the treated portion 116. In the second block 1204 of the process 1200, the biomolecule is deposited onto the linking layer through exposing the linking layer to a second plasma jet and the bio molecule. International Publication Nos. WO2020099434A1, WO2019243631A1, and WO2019038378A1, all naming Molecular Plasma Group SA as the Applicant, discuss surface treatment processes considered herein and are hereby incorporated by reference herein in their entireties.

The surface treatment processes contemplated herein may be implemented on any treated portion 116 to reduce foreign body response, among other things. In one aspect of this disclosure, the biomolecule deposited on the linking layer may include phosphorylcholine in order to mimic the natural chemistry of a cell's phospholipid membrane. In this example, a reactive phosphorylcholine species (such as acrylate-functionalized phosphorylcholine) is dispersed into a gas stream and then combined with cold, atmospheric plasma. The reactive species/plasma is directed onto the treated portion 116 to be modified as the plasma-activated surface reacts with the phosphorylcholine species, thereby creating covalent bonds and yielding a surface that is chemically functionalized with phosphorylcholine moieties. An exemplary phosphorylcholine species in accordance with one illustrated aspect herein is:

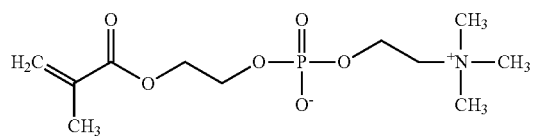

The above-described process may provide increased efficiency as to the amount of phosphorylcholine required, that is compared to a dip-coating process, among others. Further, it should be appreciated that all exposed surfaces of the treated portion 116 could be functionalized in one pass without adding a layer of material that might seal off any desirable apertures.

In one aspect of this disclosure, the biomolecule deposited on the linking layer may include hyaluronic acid. Hyaluronic acid is a molecule that may be effective in reducing foreign body response, among other things. More specifically, any treated portion 116 presenting hyaluraonic acid may avoid activating the macrophages responsible for initiating the foreign body response. In one example, a reactive hyaluraonic acid species is dispersed into a gas stream and then combined with cold, atmospheric plasma. The reactive species/plasma is directed onto the treated portion 116 to be modified as the plasma-activated surface reacts with the hyaluraonic acid species creating covalent bonds and yielding a surface that is chemically functionalized with hyaluraonic acid moieties. One illustrative example of a hyaluraonic acid species in accordance with the present disclosure is:

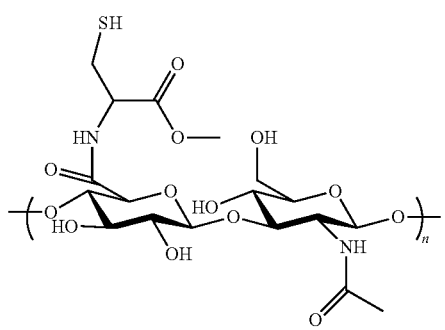

In one embodiment, the biomolecule polymer may be a biopolymer or biocompatible polymer. The polymer may be a homopolymer or a copolymer. An example of a biopolymer may include a glycosaminoglycan or mixtures thereof. Glycosaminoglycans are naturally occurring polysaccharides containing disaccharide repeating units of hexosamine and hexose or hexuronic acid, and may contain one or more sulphate groups or be non-sulphonated. Typically, the Glycosaminoglycan is non-sulphonated. The Glycosaminoglycan may be anionic, or cationic, or non-ionic. Typically, the Glycosaminoglycan is anionic. In one specific embodiment, the Glycosaminoglycan is an anionic, non-sulphonated Glycosaminoglycan or mixtures thereof.

This disclosure contemplates using Glycosaminoglycan having any known size, type, or form. The molecular weight of the Glycosaminoglycan may range from about 5,000 to about 20,000,000, from about 10,000 to about 12,000,000, or from about 1,000,000 to about 10,000,000 Da (Daltons), among other ranges.

Glycosaminoglycan may be provided in free acid or salt form. The glycosaminoglycate may be associated with any suitable cation, including, but not limited to, alkali metals, such as sodium and potassium, alkaline earth metals, nitrogen-containing cations, such as ammonium, substituted ammonium and quaternized derivatives thereof, and other suitable cations. Preferred salts of Glycosaminoglycan and derivatives thereof include alkali metal or alkaline earth metal glycosaminoglycates. The Glycosaminoglycan may be provided in pure form, as a mixture of Glycosaminoglycan with proteins and naturally occurring substances derived by the production of Glycosaminoglycan from natural material, or as a chemically modified, Glycosaminoglycan derivative. Mixtures of such glycosaminoglycans may also be provided.

Representative glycosaminoglycans include hyaluronan or derivatives thereof, such as hylan, heparin, heparin, chondroitin, keratin, dermatan, and sulfates of such materials. A particularly preferred Glycosaminoglycan is hyaluronan, and derivatives thereof, which contain repeating disaccharide structure of D-glucuronic acid and 2-acetamido-2-desoxy-D-glucose joined by alternating β1→3 glucuronidic and β1→4 glucosaminidic bonds. Representative hyaluronan and derivatives thereof which may be provided include, but are not limited to: BIOMATRIX® hyaluronan provided by Biomatrix, Inc., such as described in U.S. Pat. No. 4,303,676 (Balazs) which is incorporated herein by reference, HYLADERM® hylan provided by Biomatrix, Inc., such as described in U.K. Published Patent Application No. 2,172,295A (Balazs, et al.) which is incorporated herein by reference; and substantially pure hyaluronan such as described in U.S. Pat. No. 4,141,973 (Balazs) which is incorporated herein by reference.

In some embodiments, the polymer may be biocompatible. A biocompatible polymer may be polymer having a phospholipid group, typically a phosphorylcholine group. The presence of the phospholipid group may mimic the natural chemistry of a cell's phospholipid membrane.

The biomolecule polymer may be any hydrophilic polyalkylene glycol polymer as well, at least in some embodiments. This biomolecule polymer may be PEG, or related PEG-like polymers with different architectures (networked, branched, dendritic, hyperbranched, etc.)

In another example, the biomolecule polymer may include methacrylated HLA such as:

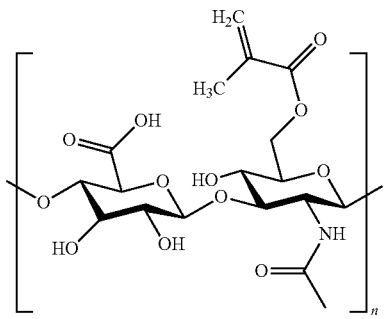

In some embodiments, the biocompatible polymer may be obtained/obtainable by synthesizing a monomer having a phosphorylcholine structure and polymerizing it with an (meth)acrylic monomer. In the case of a (meth)acrylic ester monomer, the alkyl ester of acrylic acid and methacrylic acid alkyl esters of 1 to 20 carbon atoms may be used. In the case of copolymer production, or (meth)acrylic ester monomer, the alkyl ester of acrylic acid and methacrylic acid alkyl esters of 1 to 8 alkyl esters may typically be used. Specific examples of the (meth)acrylic ester monomer include methyl acrylate, ethyl acrylate, butyl acrylate, 2-ethylhexyl acrylate (2-ethylhexyl acrylate), lauryl acrylate, and stearyl, the alkyl ester of methacrylic acid and methyl methacrylate for example methyl methacrylate, ethyl methacrylate, butyl methacrylate, 2-ethylhexyl methacrylate (2-ethylhexyl methacrylate), lauryl methacrylate, and stearyl methacrylate. As used herein, the term "(meth)acrylic" is intended to refer to acrylic or methacrylic, typically acrylic being typical for biological applications.

In various embodiments, the biocompatible polymer may have a molecular weight of about 5,000 to about 20,000,000, from about 10,000 to about 12,000,000, or from from about 1,000,000 to about 10,000,000 Da (Daltons).

While phosphorylcholine and hyaluraonic acid are specifically discussed herein as being part of the biomolecule deposited on the linking layer during the surface treatment process, this disclosure contemplates other molecules as well. For example, other peptides, proteins, polysaccharides, and hydrophilic polymers (such as poly(ethylene oxide)) are also considered herein for biomolecules to be deposited on the linking layer during the surface treatment process.

Figure 13:
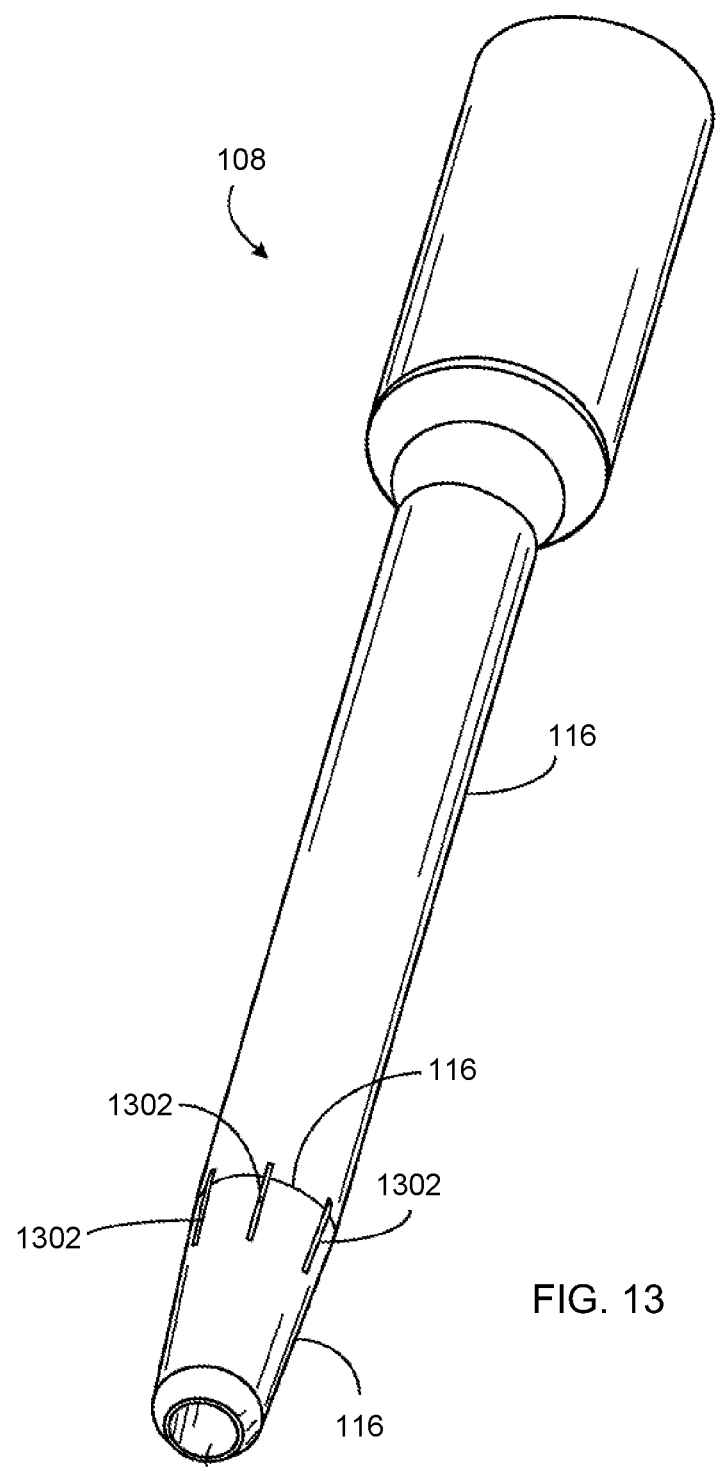
FIG. 13 is a perspective view of an embodiment of a subcutaneous device having one or more apertures or slits defined therethrough.

Referring now to FIG. 13, one embodiment of a subcutaneous device considered herein includes a cannula 108 that has a plurality of apertures or slits 1302 defined therethrough. The apertures or slits 1302 may be configured to deliver a flow path for medicament or the like through the cannula 108 to the user. The apertures or slits 1302 may be laser cut into the cannula 108 through the treated portion 116. While dip-coating the cannula 108 of FIG. 13 is one possible way of introducing the coating onto its surface, such a process can potentially result in the coating sealing the apertures or slits 1302, thereby impacting their ability to function as intended. Accordingly, the present disclosure also envisions the surface treatment process 1200 as discussed herein, which instead utilizes the cold atmospheric plasma process to surface treat the cannula 108 at the molecular level. Such a process can be implemented without the risk of sealing any apertures or slits 1302 in the cannula 108.

In some embodiments, the surface treatment process includes introducing an phosphorylcholine species (such as acrylate-functionalized phosphorylcholine) to the treated portion 116. The surface treatment process may involve introducing other phosphorylcholine species or other phospholipid materials as the biomolecule to the treated portion 116 as well. In some embodiments, the hydrophilic material includes, e.g., polyvinyl chloride (PVC) plasticized with dioctyl terephthalate (bis(2-ethylhexyl) benzene-1,4-dicarboxylate or di(2-ethylhexyl) terephthalate, (DOTP) or (DEHT), respectively. In some embodiments, the hydrophilic material incorporated into a TPE may include a polyolefin based synthetic thermoplastic polyolefin elastomer containing a hydrophilic additive.

In some embodiments, the treatment process may introduce a hydrogel material including polyvinylpolypyrrolidone (PVPP) and/or polyvinylpyrrolidone (PVP) to the treated surface 116 as the biomolecule. In some embodiments, a silver or silver chloride material may be any one or more of those described in U.S. application Ser. No. 11/194,951 and U.S. Pat. No. 6,451,003, each of which are incorporated herein by reference in their entireties.

Figure 7:
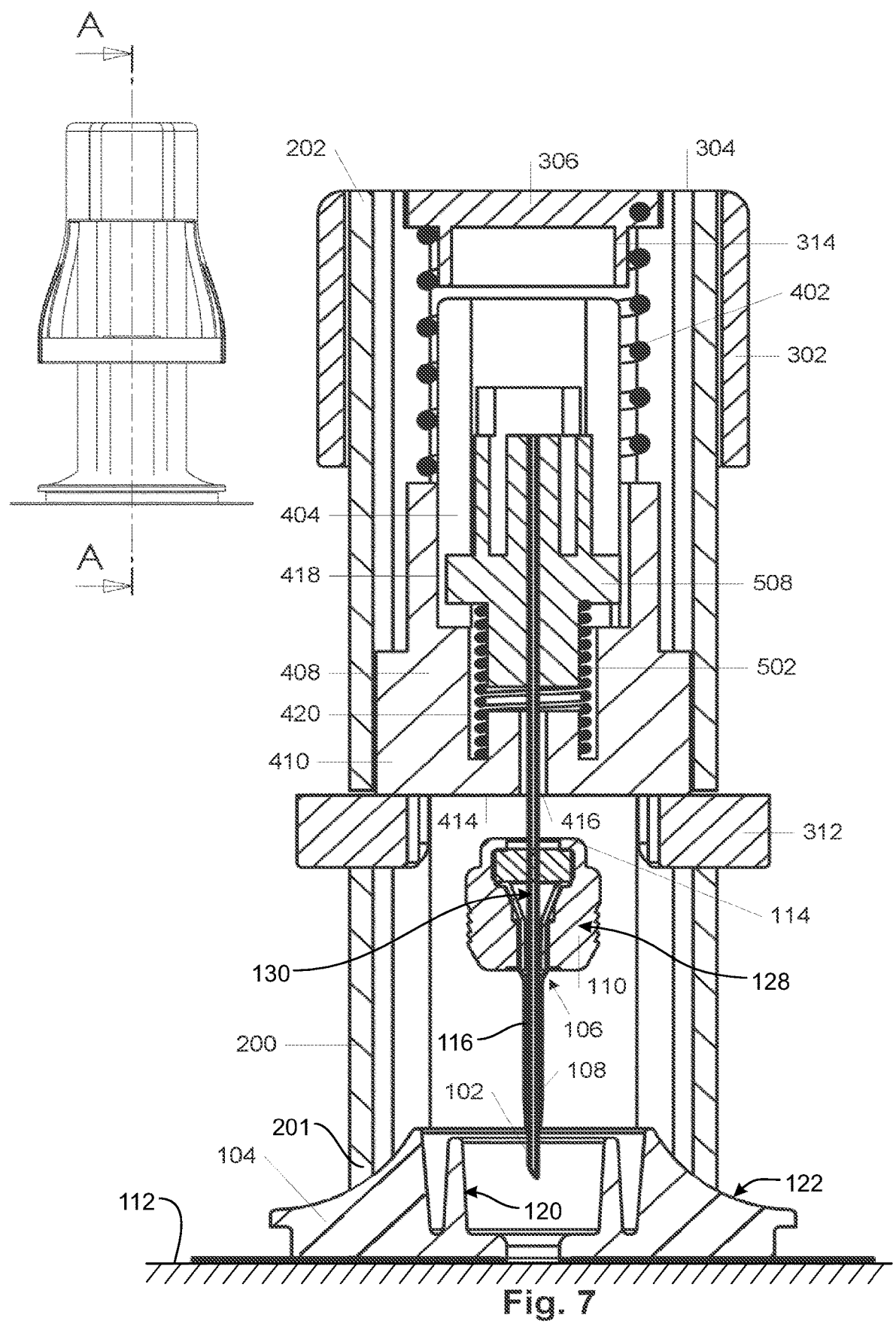
FIG. 7 is a sectional view of the inserter device of FIG. 1 in a shelf position.
Figure 8:
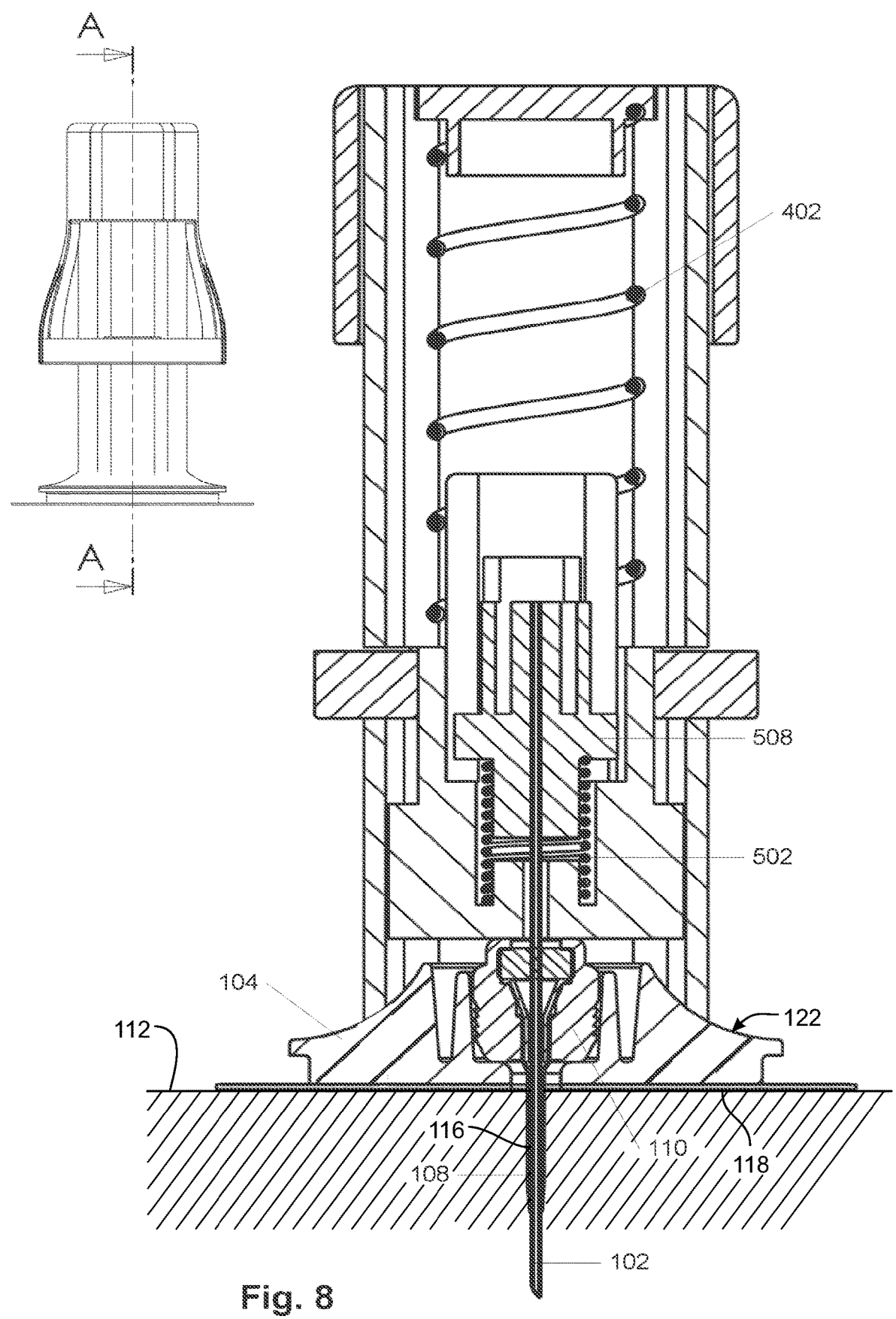
FIG. 8 is a sectional view of the inserter device of FIG. 1 in an inserted position.
Figure 9:
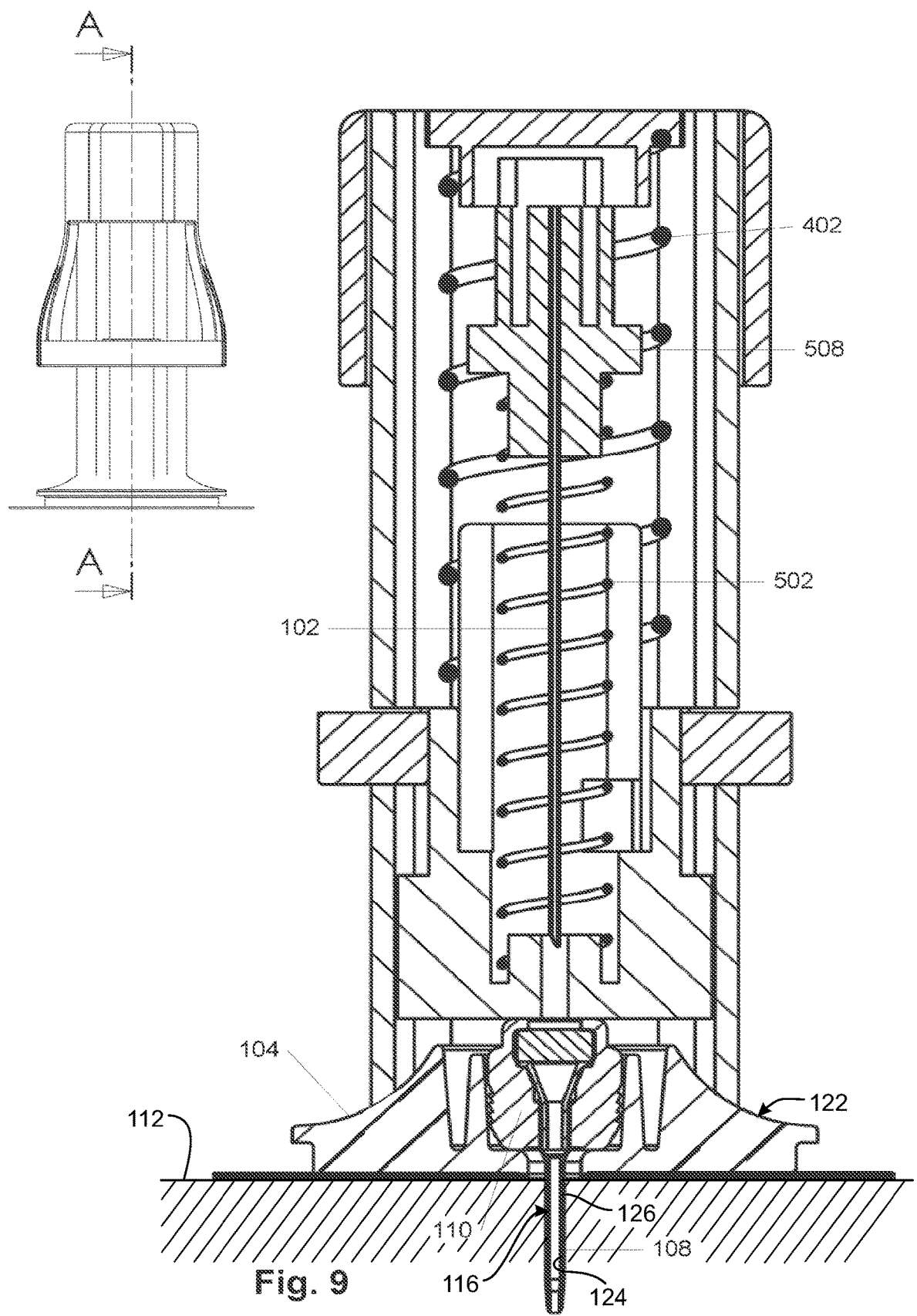
FIG. 9 is a sectional view of the inserter device of FIG. 1 in a retracted position.

In FIGS. 7-9, the inserter device 100 is displayed in a cut-through view along line AA. In some embodiments, the four parts of the inserter device 100 (i.e., the housing 200, the outer part 300, the first part 400, and the second part 500) are constructed from a hard plastic possibly combined with sections of a softer material to prevent the parts from breaking during activation of the inserter device 100. The insertion spring 402 and the retraction spring 502 may have a metallic construction, but other types of materials could also be used.

FIG. 7 shows the inserter device 100 in a shelf state before activation of the inserter device 100. Both springs 402, 502 are in a pre-loaded position. The insertion spring 402 and first part 400 are secured in the pre-loaded shelf position by the locking elements 312, which prevent the first part 400 from being displaced in relation to the housing 200. The second part 500 is kept in the pre-loaded shelf position by the locking members 508, 508', which are engaging with the two openings 418 and the support rim 419 on the inside of the first part 400. The pre-loading of the two springs 402, 502 in the shelf state ensures an advantageous compact design of the inserter device 100.

FIG. 8 shows the inserter device 100 in the inserted position in which the cannula 108 has been inserted into the patient's skin 112 and the body part 110 is secured inside the port site 104. The port site 104 includes a proximal surface 118 configured to contact the patient's skin 112. In some embodiments, the treated portion 116 is positioned on the proximal surface 118 of the port site 104.

As shown in FIG. 7, the port site 104 includes inner surfaces 120 and an outer surfaces 122. The inner surfaces 120 include the surfaces arranged to surround the body part 110 when the body part 110 is inserted in a cavity of the port site 104. The inner surfaces 120 also include the surfaces which define an opening in the port site 104 through which the cannula 108 extends. The remaining surfaces of the port site 104 define the outer surfaces 122 (including the proximal surface 118). The treated portion 116 may include any one or more of the surfaces 120 and the surfaces 122 of the port site 104.

Referring now to FIG. 9, the cannula 108 includes an inner surface 124 and an outer surface 126. The inner surface is configured to contact the insertion needle 102 to maintain the insertion needle 102 in position due to the friction therebetween as described above. The outer surface 126 is positioned opposite the inner surface 124. The treated portion 116 may be positioned on one or both of the inner surface 124 and the outer surface 126 of the cannula 108.

As shown in FIG. 7, the body part 110 may include outer surfaces 128 including a ribbed portion configured to maintain the body part 100 within the cavity of the port site 104. Further, the body part 110 may include inner surfaces 130 configured to receive an external device such as an injection needle or a supporting structure thereof. The treated portion 116 may include any one or more of the surfaces included in the inner surfaces 130 and the outer surfaces 128 of the body part 110.

In some embodiments, the port site 104 includes an adhesive surface, which may be used for attaching the port site 104 releasably to the patient's skin 112. A release paper may be removed from the port site 104 prior to placing it on the patient's skin 112. In such embodiments, the adhesive material may be part of the treated portion or may be separate and/or distinct from the treated surface.

In the inserted position shown in FIG. 8, the insertion needle 102 is still inserted in the patient, thus it has not yet returned to a retracted position. The insertion spring 402 is in a relaxed position, whereas the retraction spring 502 is still in the pre-loaded position.

FIG. 9 shows the inserter device 100 in a retracted position after the cannula 108 has been inserted into the patient's skin 112 and the insertion needle 102 attached to the second part 500 has been retracted to a position at the distal end 205 of the housing 200 such that the insertion needle is no longer positioned inside the first part 400. The retraction spring 502 is in the relaxed position in which it cannot be re-loaded again without breaking apart the inserter device 100. This ensures that the insertion needle 102 is contained inside the inserter device 100 and unable to extend outside of it.

Insertion of the subcutaneous part 106 into a patient's skin 112 is done by placing the inserter device 100 on the patient's skin 112 with the port site 104 positioned directly on top of the patient's skin 112, and then activating the inserter device 100. Typically, a protective release paper has to be removed from the port site 104 prior to placing it on the patient's skin 112, thereby exposing an adhesive layer underneath the port site 104 for fastening the port site 104 to the patients skin 112.

Activation of the inserter device 100 is done by applying a pressure on the two release elements 308 on the outer part 300, i.e. deforming the engaging device 310 by pressing the two release elements 308 closer together. The distance between the locking elements 312 thereby increases such that there is enough space to allow for the locking members 410 on the first part 400 to pass by the locking elements 312 at the aid of the insertion spring 402, the latter which in this manner is allowed to relax.

The clock-wise turning of the second part 500 prompt by the housing guide member 206 progressing inside the slit 412 and turning the inclining guide member 510 is observable when comparing FIGS. 10A-C and FIGS. 11A-C, in particular the FIGS. 10A-B and FIGS. 11A-B. The release of the locking members 508, 508' from the inner openings 418 is seen most clearly in the FIGS. 10C and 11C, where FIG. 10C shows the locking members 508, 508' being secured underneath the inner openings 418, and FIG. 11C shows the locking members 508, 508' positioned in the releasing slits 406 in first part 400, allowing the retraction spring 502 to relax and thereby push the second part 500 to an extracted position, where it is no longer contained inside the first part 400.

The second part 500 is normally turned 10-40 degrees in relation to the first part upon release of the second part 500 form the first part 400.

The inserter device 100 is constructed such that it can only be used once, since it is impossible to re-load the springs 402, 502 after activation of the inserter device 100. This is advantageous as the user cannot be tempted to use the device more than once and thereby expose himself/herself to an unnecessary health risk.

Construction of the inserter device 100 from essentially four interconnected parts 200, 300, 400, 500 combined with two springs 402, 502 and an insertion needle 102 allows for a simple construction, whereby a rather compacted device is obtained. This reduces production costs.

Normally, the inserter device 100 is contained in a protective bag during transportation. The conditions inside the bag are sterile ensuring that the inserter device 100 can be kept sterile up until the time where it is going to be used. The only time, the inserter needle 102 is exposes is in the brief moment of insertion. This makes the inserter device 100 safe to handle as the user cannot get in contact with the insertion needle 100 prior to activation of the device and/or after the automatic retraction of the insertion needle 100. It is thereby safe to dispose the inserter device 100 along with ordinary household waste without protecting it beforehand.

The automatic insertion and automatic retraction of an insertion needle 102, prompted by applying a pressure in the horizontal plane, is easy to perform by the user, since it essentially involves one action. Further, as the insertion process does not involve applying a pressure in the direction towards to skin, the procedure is more appealing to users that have a fear of injection needles and other penetrating devices, as these users often find it significantly more difficult to insert an insertion needle if they have to apply a pressure towards the skin at the same time.

Various plasma coating types (e.g., PEG, Phosphorocholine (PC), and Hyaluronic acid (HLA)) were applied onto PTFE cannulas. The results are summarized in Table 1 below.

TABLE 1

| Sample # | Coating Type | Precursor | Sheet WCA [°] | Canula WCA [°] |
|---|---|---|---|---|
| 0 | None | untreated | 105-110 | 113-115 |
| 1 | PEG | 3EGDVE | 27-28 | 81-84 |
| 2 | PEG | Activation 3EGDVE | 27-28 | N/A |
| 3 | PC | MA-PC | 40-45 | 91-92 |
| 4 | PC | MA-PC | 40-45 | N/A |
| 5 | PC | MA-PC | 45-50 | 72-75 |
| 6 | PC | Activation MA-PC | 40-45 | 80-83 |
| 7 | HLA | HAM-201c/ EGDMA | 33-45 | 85-87 |
| 8 | HLA | HAM-201c/ EGDMA | 39-45 | N/A |
| 9 | HLA | HAM-201c/ EGDMA | 38-42 | 80-81 |
| 10 | HLA | Activation HAM-201c/ EGDMA | 40-43 | 82-84 |

3EGDVE = Tri(ethylene glycol) divinyl ether (CAS 765-12-8)
EGDMA = Ethylene glycol dimethacrylate (CAS 97-90-5)
MA-PC = 2-Methacryloyloxyethyl phosphorylcholine (CAS 67881-98-5) 10 wt % in EGDMA/EtOH 50/50
HAM-20k = Hyaluronic acid methacrylate (Mw 20,000-30,000) 2 wt % in $H_2O$
Activation: 8 slm $CO_2$ in 80 slm $N_2$-5 b-a-f - Plasma power = 450 W 3EGDVE=Tri(ethylene glycol) divinyl ether (CAS 765-12-8). Precursor for the plasma deposition of anti-fouling PEG-like coatings. 3EG units. Vinyl groups tend to enhance grafting and deposition rate.

MA-PC=2-Methacryloyloxyethyl phosphorylcholine (CAS 67881-98-5) 10 wt % in EGDMA/EtOH 50/50. Methacrylate-functionalized phosphorylcholine. Suggested by ConvaTec, to mimic cell walls. MA-PC was poorly soluble in EGDMA (crosslinker). It was very soluble in ethanol. It was then decided to dissolve 10 wt % of MA-PC, in a 50/50 (wt) mixture of EGDMA and ethanol. Plasma deposition of this formulation should lead to a MA-PC-rich, EGDMA-based plasma-polymer matrix.

HAM-20k/EGDMA=HAM-20k=Hyaluronic acid methacrylate (Mw 20,000-30,000) 2 wt % in $H_2O$. HAM-20k was only soluble in water. We also tried to dissolve it in EtOH and EGDMA, unsuccessfully. It was then decided to co-inject the HAM-20k solution and EGDMA, using separate atomizers simultaneously. Plasma co-deposition of the water-based HAM-20k solution and EGDMA should lead to a HAM-20k-rich, EGDMA-based plasma-polymer matrix.

UV1 and UV2=Rhodamine 6G (R6G) was used as UV-tracer for Q&D testing. The UV1 solution was prepared by adding 0.1 wt % of R6G in a 3EGDVE/EtOH 90/10 (wt) solution. Addition of EtOH was necessary to completely dissolve R6G. The UV2 solution was prepared by adding 1 wt % of R6G in a EGDMA/EtOH 80/20 (wt) solution.

MPG's PlasmaSpot® equipment was used for all treatments (see FIG. 2). A specific nozzle, designed and printed by MPG (ref: 20 000106), enabled uniform treatment of the outer walls of the cannulas. Cannulas were mounted on a rotating (ca. 5 RPM) sample holder system by means of a long, gauge 27 needle (OD=0.4 mm) passing through the cannula. The plasma head was then scanned across the surface to be treated.

The plasma power was fixed to 300 W in the case of 3EGDVE (see experimental table above). This value should lead to optimal grafting and highest crosslinking degree of the PEG-like plasma coating. For the MA-PC and HAM-20k/EGDMA cases, two different plasma power settings were tested: 300 W and 450 W.

Line speed was arbitrarily set to 0.6 m/min, and the number of passes (→coating thickness) was arbitrarily set to a relative high value of 20 (10 back-and-forth scans). Coating thickness can be optimized at a later stage of the research.

The mass feed of the precursor was controlled by the "precursor flow" parameter. This parameter was fixed in the 3EGDVE case to the already known optimal precursor feed, while it was varied in other cases. Nitrogen ($N_2$;80 slm) was the main plasma and carrier gas.

The power-to-precursor feed ratio, in other words the energy-per-molecule, influences the retention of key chemical moieties along with the degree of cross-linking. While higher power potentially induces a more cross-linked and better grafted plasma-coating, it also leads to more fragmentation of the precursor, thus, a loss of chemical moieties.

"Sheet WCA" were measured immediately after treatment, on flat PTFE sheets that underwent the same treatment as the cannulas. "Cannula WCA" were measured on the cannulas themselves. Cannulas were stored in the lab for approximately 7 months between treatment and measurement.

Q&D Testing:

Several tests were performed at MPG, during the Discovery Day. A portable water contact angle (WCA) equipment was used to evaluate the hydrophilicity of treated model PTFE surfaces (PTFE tape). In addition, as requested by ConvaTec, extra sacrificial samples (with UV tracer) were produced to evaluate the homogeneity and resistance of the coatings to the silicone block penetration test.

WCA: The values are reported in the experimental table, for every precursor and condition tested.
Untreated PTFE tape: 105-110°; $CO_2$-activated PTFE tape: 85-90°.
3EGDVE led to WCA values around 27-28°, regardless of the activation step,
MA-PC-based coatings led to angles in the 40-45° range. Higher power and higher precursor flow condition #5 led to a slight increase in WCA, 45-50°.

HAM-20k: condition #7 (medium power, lower precursor flow) led to WCA in the 33-35° range. Increasing power and precursor flow led to a slight increase in WCA, 40-45°.

IMPORTANT NOTE: we re-checked the WCA values after wetting-drying of the samples. The measured WCA values remained in the same range as for the freshly-treated ones. This is an indication that the plasma coatings are well-grafted, and do not release/dissolve upon humidification or, to the least, not completely.

Qualitative "silicone block" test: Extra samples were prepared using UV tracer-doped chemical precursors (UV1 and UV2, see Experimental section). The UV-tracer enabled assessing the uniformity of the coatings, and their resistance to penetration in a silicone block. As shown in FIG. 3, both PEG-like and EGDMA types of plasma coatings exhibited remarkable resistance to penetration, even in absence of $CO_2$ plasma activation.

CONCLUSIONS

Successful deposition of all types of chemistries; all conditions led to persistently wettable surfaces.

The silicone block test has shown very good resistance of the coatings to penetration, even in absence of the plasma pre-activation step. This was judged very promising by ConvaTec.

Samples to be tested at ConvaTec have been produced as follows:

20 replicates (9 mm cannulas) for the PEG-like coatings, conditions #1 and #2.

6 replicates (6 mm cannulas) per condition for the other two chemistries (MA-PC and HAM-20k).

3 replicates of UV1- and UV2-type coatings have also been included in the package (6 mm cannulas).

In total, 94 cannulas were treated and will be tested by ConvaTec.

While this disclosure has been described with respect to at least one embodiment, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A method of modifying a medical device, the method comprising:

treating a portion of the medical device with cold plasma; and functionalizing the plasma-treated portion with a polymer, wherein the polymer comprises a hyaluronic acid species, and wherein the polymer comprises a compound comprising the formula:

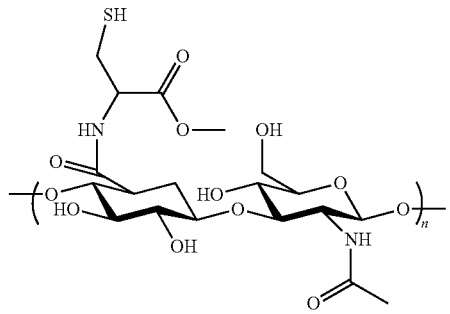

Formula (II)

2. The method of claim 1, wherein the plasma-treated portion of the medical device is disposed at least partially along a surface of a subcutaneous part of the medical device that is configured for subcutaneous positioning in a user.

3. The method of claim 1, wherein the plasma-treate portion of the medical device is at least partially defined along a surface of a cannula and configured for subcutaneous positioning in a user.

4. The method of claim 1, wherein:

treating the portion of the medical device includes treating the portion at temperatures of about 0-60 degrees Celsius and at pressures of around 1 atmosphere; and functionalizing the plasma-treated portion with the polymer includes functionalizing the plasma-treated portion simultaneously with treating the portion of the medical device.

5. The method of claim 1, wherein:

the polymer comprises one or more hydrophilic polyalkylene glycol polymers;

the one or more hydrophilic polyalkylene glycol polymers include PEG or related PEG-like polymers with different architectures; and the architectures are one or more of networked, branched, dendritic, or hyperbranched.

6. A method of modifying a medical device, the method comprising:

treating a portion of the medical device with cold plasma;

functionalizing the plasma-treated portion with a polymer; and immobilizing a biomolecule through a linking molecule located on a surface of the plasma-treated treated portion, wherein:

immobilizing the biomolecule through the linking molecule includes generating and maintaining a non-thermal atmospheric pressure plasma at a temperature at or below about 60° C., the linking molecule is deposited onto the plasma-treated portion by exposing the plasma-treated portion to a first plasma jet and the linking molecule to generate a linking layer on the plasma-treated portion, the method further comprises depositing the biomolecule onto the linking layer by exposing the linking layer to a second plasma jet and the biomolecule, the biomolecule comprises a hyaluronic acid species, and the biomolecule comprises a formulation compound comprising the formula:

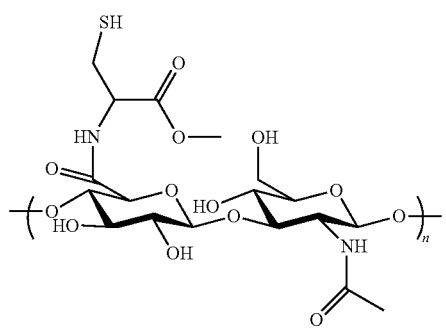

Formula (II)

7. A method of manufacturing a medical device, the method comprising:
   providing a subcutaneous part configured to be positioned subcutaneously in a user;
   performing a surface treatment on a portion of the subcutaneous part, and
   forming one or more apertures through the subcutaneous part prior to performing the surface treatment on the portion of the subcutaneous part,
   wherein performing the surface treatment on the portion of the subcutaneous part includes
      exposing a treated portion of the subcutaneous part to cold atmospheric plasma to create a linking layer thereon and
      functionalizing the linking layer with a biomolecule configured to reduce a foreign body response to the subcutaneous part when the subcutaneous part is subcutaneously positioned in the user,
   and wherein performing the surface treatment on the portion of the subcutaneous part does not close the one or more apertures.

8. The method of claim 7, wherein the biomolecule comprises a phosphorylcholine species.

9. The method of claim 8, wherein the biomolecule comprises a compound comprising the formula:

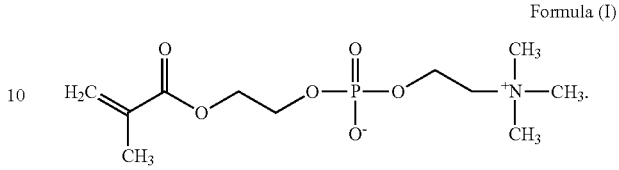

Formula (I)

10. The method of claim 7, wherein the biomolecule includes a hyaluraonic acid species.

11. The method of claim 10, wherein the biomolecule comprises a compound comprising the formula:

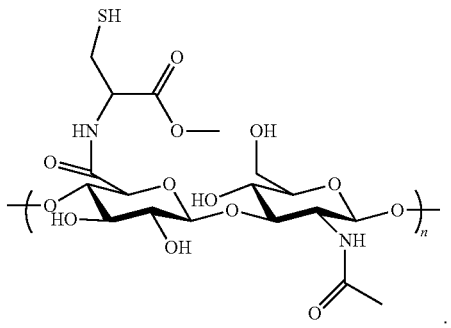

Formula (II)

* * * * *

UNITED STATES PATENT AND TRADEMARK OFFICE
CERTIFICATE OF CORRECTION

PATENT NO. : 11,890,642 B2
APPLICATION NO. : 17/564586
DATED : February 6, 2024
INVENTOR(S) : Neal Robert Carty It is certified that error appears in the above-identified patent and that said Letters Patent is hereby corrected as shown below:

In the Claims

Claim 3 at Column 22, Line 21:
Delete "plasma-treate" and insert --plasma-treated--.

Signed and Sealed this
Twelfth Day of March, 2024

Katherine Kelly Vidal
Director of the United States Patent and Trademark Office